United States Patent [19]

Nakagawa et al.

[11] Patent Number: 4,482,629

[45] Date of Patent: Nov. 13, 1984

[54] LIGHT-SENSITIVE SILVER HALIDE COLOR PHOTOGRAPHIC MATERIAL

[75] Inventors: Satoshi Nakagawa; Hiroshi Sugita; Shuzi Kida; Morito Uemura, all of Hino; Ken-ichi Kishi, Hachioji, all of Japan

[73] Assignee: Konishiroku Photo Industry Co., Ltd., Tokyo, Japan

[21] Appl. No.: 475,857

[22] Filed: Mar. 16, 1983

[30] Foreign Application Priority Data

Mar. 20, 1982 [JP] Japan ................................. 57-45809

[51] Int. Cl.$^3$ .............................................. G03C 7/26
[52] U.S. Cl. ................................... 430/542; 430/544; 430/548; 430/550; 430/551; 430/553; 430/558; 430/955; 430/957; 430/960
[58] Field of Search ............... 430/382, 385, 543, 544, 430/548, 550, 551, 553, 558, 955, 957, 960, 542

[56] References Cited

U.S. PATENT DOCUMENTS

| | | | |
|---|---|---|---|
| 3,214,437 | 10/1965 | Loria et al. | 430/474 |
| 3,227,551 | 1/1966 | Barr et al. | 430/553 |
| 4,028,106 | 6/1977 | Hori et al. | 430/385 |
| 4,042,393 | 8/1977 | Wada et al. | 430/385 |
| 4,052,212 | 10/1977 | Deguchi et al. | 430/553 |
| 4,072,525 | 2/1978 | Inouye et al. | 430/385 |
| 4,248,962 | 2/1981 | Lau | 430/553 |
| 4,310,618 | 1/1982 | Fernandez et al. | 430/548 |
| 4,390,618 | 6/1983 | Kobayashi et al. | 430/553 |
| 4,409,323 | 10/1983 | Sato et al. | 430/544 |

Primary Examiner—J. Travis Brown
Attorney, Agent, or Firm—Frishauf, Holtz, Goodman & Woodward

[57] ABSTRACT

There is disclosed a light-sensitive silver halide photographic material containing a compound represented by the formula (I):

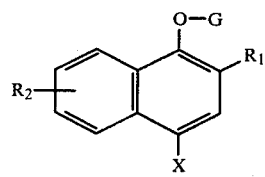

Formula (I)

wherein G, $R_1$, $R_2$ and X have the same meanings as defined in the specification.

The 1-naphthol coupler which is contained in the light-sensitive silver halide photographic material is high in reactivity with an oxidized product of a color forming developing agent and can efficiently impart imagewise photographic effects to light-sensitive silver halide photographic materials.

20 Claims, No Drawings

LIGHT-SENSITIVE SILVER HALIDE COLOR PHOTOGRAPHIC MATERIAL

This invention relates to a light-sensitive silver halide color photographic material containing a 1-naphthol coupler which is high in reactivity with an oxidized product of a color forming developing agent and good in alkali solubility of the cyan dye formed by the coupling reaction.

In recent years, light-sensitive silver halide color photographic materials are increasingly desired to be made higher in sensitivity or smaller in film format. Accompanied with this tendency, in order to provide higher image quality (particularly graininess, sharpness) than those of the prior art, it is very important to impart various photographic effects to the light-sensitive materials without affecting deleterious effects thereon during exposure or development processing.

Various techniques have been known for improvement of image quality of light-sensitive silver halide photographic materials. For example, U.S. Pat. No. 3,227,554 discloses a technique by use of Development Inhibitor Releasing Coupler (DIR Coupler) in which a development inhibitor is released imagewisely from the coupling position (site) of a coupler for photography through the reaction between a coupler for photography and an oxidized product of a color forming developing agent to improve graininess and sharpness by intra-image effect and inter-image effect. Also, in Japanese Provisional Patent Publication No. 150845/1982, there is disclosed a Development Accelerator Releasing Coupler (DAR Coupler) which enables improvement of sensitivity with the use of a microparticulate silver halide emulsion as the result of enhancement of efficiency in development of silver halide through imagewise releasing of a development accelerator from a coupler for photography with the progress of development.

On the other hand, in U.S. Pat. No. 4,248,962, Japanese Provisional Patent Publications No. 114946/1981 and No. 154234/1982, there are disclosed couplers which enable control of a number of parameters such as controlling in time or distance the effects by photographically useful groups, by releasing in the first step a timing group accompanied with a photographically useful group (e.g. developmnt inhibitor) from the coupling position of a coupler for photography through the reaction with a coupler for photography and an oxidized product of a color forming developing agent and then releasing in the second step a photographically useful group (e.g. development inhibitor) as the final desired product through the intramolecular reaction of the timing group. Such a compound having a photographically useful group substituted through a timing group at the coupling position of a coupler for photography, which can control variously the photographic effects exhibited by photographically useful groups, is very advantageous in designing of light-sensitive materials as compared with a compound having a photographically useful group substituted directly at the coupling position such as the DIR Coupler or the DAR coupler as mentioned above. However, most of these compounds, since they have ballast groups in the couplers for photography, form imagewise alkali-insoluble products (i.e. dyes) through the reaction with an oxidized product of a color forming developing agent, which remain in photographic elements. As the result, in case of a light-sensitive material utilizing a non-diffusible color image, when employed in coupler containing layer with different color phases, there is involved a vital defect that color turbidity occurs which is not favorable in color reproduction. For this reason, when these compounds are used, it is required to select a compound which can form the same color phase as the dye formed by a coupler for photography to be contained in the layer employed, whereby designing of a light-sensitive material has been greatly restricted.

Whereas, there is also known a compound which itself is converted to a colorless product through the reaction with an oxidized product of a color forming developing agent simultaneously with imparting a photographic effect. For example, no color indicating DIR Coupler as disclosed in U.S. Pat. Nos. 3,632,345 and 3,958,993 is converted to a colorless product through the coupling reaction with release of a development inhibitor capable of giving the same photographic effect as the DIR Coupler as described above. Also, the no color indicating coupler as disclosed in U.S. Pat. No. 3,876,428 and Japanese Provisional Patent Publication No. 152721/1977, by utilizing the property to be converted to a colorless product through the coupling reaction, captures an excessive amount of an oxidized product of color forming developing agent for preventions of color turbidity and fogging. These compounds, which are converted to colorless products through the reaction with oxidized products of color forming developing agents, involve no problem of color turbidity as mentioned above and favorable with respect to broadened width of choice in designing of light-sensitive materials. However, they have the drawbacks of poor reactivity with oxidized products of color forming developing agents and poor storage stability of the compounds and therefore poorly applicable in practical applications.

In U.S. Pat. No. 4,310,618, Japanese Provisional Patent Publications No. 133734/1981 and No. 135841/1981, there are disclosed so called Blocked Dye-Forming Couplers, which are converted to alkali-soluble dye products through the reaction with oxidized products of color forming developing agents simultaneously with release of new color image forming couplers. Such couplers are intended for improvement of graininess of color images through enhancement of euivalent number of couplers to 6 equivalents or 8 equivalents as the result of development of more silver halide than is required in ordinary color image forming couplers to obtain the final color images. However, in order to achieve this object, blocked couplers must be excellent in alkali solubility so that the dyes formed may not contribute to the densities of color images and also excellent in reactivity with oxidized products of color forming developing agents to readily release color image forming couplers. Open chain keto-methylene couplers disclosed in these patents involve the vital defects in that they are poor in reactivity with oxidized products of color forming developing agents and also inferior in alkali solubility of the dyes formed to cause color turbidity.

As described above, various attempts have been made to impart imagewisely photographic effects by the reaction with oxidized products of a color foming developing agent. However, all of them involves problems in reactivity, undesirable remaining of dyes formed, storage stability and others, and therefore it would be desirable to have a new technique for improvement of the image quality of a light-sensitive silver halide color photographic material.

Accordingly, a first object of this invention is to provide a coupler which is high in reactivity with an oxidized product of a color forming developing agent and can efficiently impart imagewise photographic effects to light-sensitive silver halide photographic materials.

A second object of this invention is to provide a light-sensitive silver halide photographic material containing a 1-naphthol coupler which is good in alkali solubility of the cyan dye formed by the coupling reaction with an oxidized product of a color forming developing agent.

A third object of this invention is to provide a light-sensitive silver halide color photographic material improved in image quality.

A fourth object of this invention is to provide a light-sensitive silver halide color photographic material which is good in color reproduction.

A fifth object of this invention is to provide a light-sensitive silver halide color photographic material which is good in storability with lapse of time.

The present inventors have made extensive studies and consequently accomplished the above objects by a light-sensitive silver halide color photographic material containing a compound represented by the formula (I) shown below.

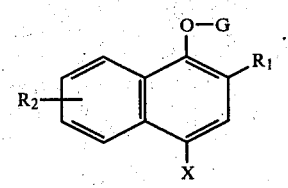

Formula (I)

wherein G represents a hydrogen or a blocking group eliminable from the compound represented by the above formula (I) through hydrolysis or intramolecular nucleophilic substitution during development; $R_1$ represents an organic group having 16 or less carbon atoms having at least one substituent group selected from carboxyl, sulfo and hydroxyl groups, which may also form a salt; $R_2$ represents a hydrogen or a water soluble acidic group; and X represents a -TIME-PUG group (where TIME represents a timing group which is eliminated together with PUG from the compound represented by the above formula (I) through the reaction of the compound represented by the above formula (I) with an oxidized prduct of a color forming developing agent and can thereafter release PUG which represents a photographically useful group), a coupler residue or a development accelerator group.

As the organic group having 16 or less carbon atoms represented by $R_1$, there may be included carbamoyl groups (e.g. alkyl carbamoyl groups, aryl carbamoyl groups, heteroxyclic carbamoyl groups, etc.), sulfamoyl groups (e.g. alkyl sulfamoyl groups, aryl sulfamoyl groups, heterocyclic sulfamoyl groups, etc.), acyl groups (e.g. alkyl carbonyl groups, aryl carbonyl groups), aryl sulfonyl groups, aryl groups or heterocyclic groups containing at least one substituent group selected from carboxyl, sulfo and hydroxyl groups.

As the water soluble acidic group represented by $R_2$, there may be included carboxyl, sulfo, carboxyalkyl, sulfoalkyl and carboxylalkylamino groups.

As an example of the above timing group, there may be included those capable of releasing PUG through the intramolecular nucleophilic substitution reaction as disclosed in U.S. Pat. No. 4,248,962 and Japanese Provisional Patent Publication No. 56837/1982, and those capable of releasing PUG through the electron transfer reaction along the conjugated chain as disclosed in Japanese Provisional Patent Publication Nos. 114946/1981 and 154234/1982.

The TIME useful in this invention may be inclusive of the compounds represented by the following formulae (II) (IV) and (V), by which this invention is not limited.

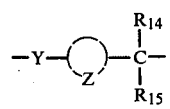

Formula (II)

wherein Z represents an atomic group necessary for completion of a benzene ring or a naphthalene ring which may have substituents; Y represents —O—, —S—or

and is bonded to the coupling position of the group (called as 1-naphthol coupler group) in the formula (I) represented by formula (III):

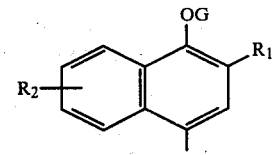

Formula (III)

(wherein G, $R_1$ and $R_2$ are the same as defined above), $R_{14}$, $R_{15}$ and $R_{16}$ represent hydrogen atoms, alkyl groups or aryl groups; and the group

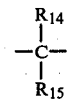

is substituted at an ortho position or a para position relative to Y and is bonded to a hetero atom contained in PUG.

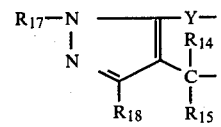

Formula (IV)

wherein Y, $R_{14}$ and $R_{15}$ are the same as defined in the formula (II), respectively; $R_{17}$ represents a hydrogen atom, an alkyl group, an aryl group, an acyl group, a sulfonyl group, an alkoxycarbonyl group or a heterocyclic group residue; and $R_{18}$ represents a hydrogen atom, an alkyl group, an aryl group, a heteroxylic group residue, an alkoxy group, an amino group, an acid amide group, a sulfonamide group, a carboxyl group, an alkoxycarbonyl group, a carbamoyl group or a cyano; this timing group being also bonded similarly as in the formula (II) through Y to the coupling position of the 1-naphthol coupler group represented by the formula (III) and to a hetero atom of PUG through the group

Next, an example of the timing group capable of releasing PUG through the intramolecular nucleophilic substitution reaction is shown by the formula (V).

Formula (V)

wherein Nu is a nucleophilic group having an oxygen, sulfur or nitrogen atom enriched in electrons and is bonded to the coupling position of the 1-naphthol coupler group represented by the formula (III); E is an electrophilic group having a carbonyl group, a thiocarbonyl group, a phosphinyl group or a thiophosphinyl group deficient in electrons and is bonded to a hetero atom of PUG; and A is a bonding group which sterically correlates Nu with E and, after Nu is released from the 1-naphthol coupler group represented by the formula (III), is subject to an intromolecular nucleophilic substitution reaction accompanied with a 3-membered to 7-membered ring formation, thereby enabling release of PUG.

As the photographically useful group PUG, there may be employed any group which can be made available in a photographic element in an imagewise pattern.

Typical examples of photographically useful groups may include, for example, development inhibitors, development accelerators, bleach inhibitors, bleach accelerators, developing agents, fixing agents, silver halide solvents, silver complexing agents, film hardeners, tanning agents, color controllers, fogging agents, antifoggants, chemical or spectral sensitizers, desensitizers, dyes or their precursors for photography, couplers (e.g. competing couplers, color forming couplers, development inhibitor-releasing couplers, namely DIR-couplers) and so on. Among the blocking groups represented by G in formula (I), representative groups eliminable through hydrolysis are acyl groups as disclosed in U.S. Pat. Nos. 2,575,182; 2,706,685; 2,865,748; and 4,123,281, including aliphatic carbonyl groups, aromatic carbonyl groups, aliphatic sulfonyl groups or aromatic sulfonyl groups. As the groups eliminable through intramolecular nucleophilic substitution, representative are those disclosed in Japanese Provisional Patent Publicataion No. 53330/1980. Such groups may be represented by the following formula:

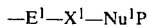

wherein $E^1$ represents an electrophilic group; $Nu^1P$ represents a precursor of a nucleophilic group convertible to a nucleophilic group under alkaline conditions; and $X^1$ represents a bonding group which sterically correlates $E^1$ with $Nu^1P$ so that an intramolecular nucleophilic substitution may occur which cleaves the bonding between $E^1$ and the oxygen atom of the 1-naphthol coupler to which $E^1$ is bonded after $Nu^1P$ has been converted to a nucleophilic group.

Particularly preferred compounds for accomplishing the objects of this invention are represented by the following formula (VI):

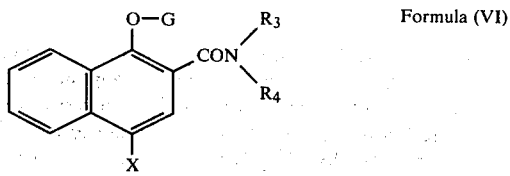

Formula (VI)

In the above formula (VI), G and X have the same meanings as in the formula (I). $R_3$ represents a hydrogen, an alkyl group having 4 or less carbon atoms (e.g. methyl, ethyl, butyl, etc.), $R_4$ represents a carboxyalkyl group, a sulfo alkyl group or a hydroxyalkyl group having 12 or less, more preferably 8 or less carbon atoms (e.g. carboxymethyl, sulfomethyl, carboxyethyl, sulfoethyl, hydroxyethyl, sulfo-2-methylpropyl, sulfo-2,2-dimethylpropyl, sulfobutyl, carboxybutyl, sulfo-4-ethylbutyl, sulfopentyl, 4-carboxymethoxybenzyl, etc.), and a phenyl group, a naphthyl group or a 5-membered or 6-membered heterocyclic group (e.g. furyl group, pyridyl group, thiazolyl group, etc.) having at least one carboxyl, sulfo or hydroxyl groups directly or through an alkylene group having 1 to 4 carbon atoms (methylene, ethylene, butylene, etc. which may be bonded through —CO—, —CONH—, —SO$_2$NH—, —NHCO—, —NHSO$_2$— or —O—) or a phenylene group. Said phenyl group, naphthyl group or 5-membered or 6-membered heterocyclic group may be further substituted with halogen atoms (e.g. chlorine, bromine, iodine, etc.), nitro, cyano, alkyl groups having 1 to 4 carbon atoms (e.g. methyl, ethyl, propyl, isopropyl, butyl, etc.), alkoxy groups having 1 to 4 carbon atoms (e.g. methoxy, ethoxy, butoxy, etc.), alkylamino groups (e.g. methylamino, dimethylamino, ethylamino, etc.) and others.

Alternatively, $R_3$ and $R_4$ taken together may form a nitrogen containing 5-membered or 6-membered ring having carboxyl, sulfo or hydroxyl group(s). These carboxyl, sulfo or hydroxyl group may be in the form of salts dissociable into ions.

In the compounds of this invention represented by the formula (I), preferable photographically useful groups represented by PUG are development inhibitor groups, development accelerator groups and coupler residues.

As the development inhibitor groups, there may be included mercaptotetrazole group, selenotetrazole group, mercaptobenzothiazole group, selenobenzothiazole group, mercaptobenzooxazole, group selenobenzooxazole group, mercaptobenzimidazole group, selenobenzimidazole group, benzotriazole goup, benzodiazole group and iodine atom, etc, as described in U.S. Pat. Nos. 3,227,554; 3,384,657; 3,615,506; 3,617,291; and 3,733,201, U.K. Pat. No. 1,450,479 and so on.

As the development accelerator groups represented by X in the formula (I), preferable are groups derived from thiourea, hydrazine, rhodanine or thioamide, particularly acylhydrazine derivative groups. More specifically, the groups represented by the following formula (VII) are preferred.

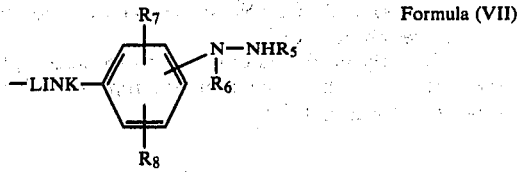

Formula (VII)

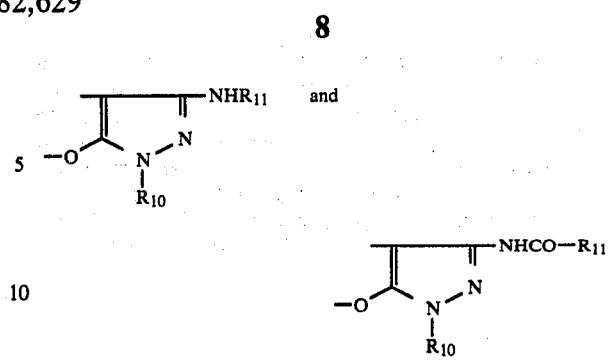

wherein LINK represents a divalent connecting group; $R_5$ represents a formyl group, an acyl group (e.g. acetyl, propionyl, trifluoroacetyl, benzoyl, etc.), a sulfonyl group (e.g. methanesulfonyl group, benzenesulfonyl group, etc.), an alkoxycarbonyl group (e.g. ethoxycarbonyl, etc.), a carbamoyl group (e.g. dimethylaminocarbonyl group, etc.) or a sulfamoyl group (e.g. dimethylamino sulfonyl group, etc.); $R_6$ represents a hydrogen atom, an acetyl group, an ethoxycarbonyl group or a methanesulfonyl group; each of $R_7$ and $R_8$ represents a hydrogen atom, a lower alkyl group (e.g. methyl, etc.), a lower alkoxy group (e.g. methoxy, etc.) or a halogen atom (fluorine, chlorine, bromine, etc.)

In the formula (VII), LINK is bonded by a hetero atom thereof to the coupler and may be a divalent group or a divalent group formed by connecting plural divalent groups selected from divalent groups such as alkylene, phenylene, alkenylene, ether, thioether, amide, thioamide, sulfonamide, ester, sulfone, urea, thiourea, heterocyclic ring, etc.

As the coupler residue represented by X in the formula (I), preferable are those represented by the following formula (VIII):

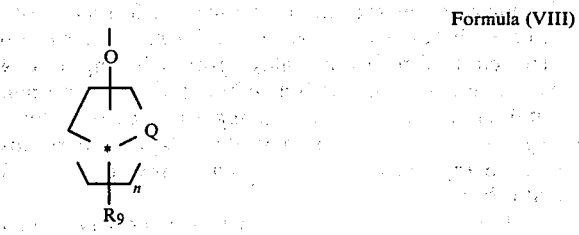

Formula (VIII)

In the above formula (VIII), Q represents a non-metallic atom necessary for completion of a 5-pyrazolone magenta dye forming coupler group or a phenol cyan dye forming coupler group together with an oxygen atom adjacent to the ring formed by Q; * in the ring completed by Q represents the coupling position; $R_9$ represents a hydrogen atom or a coupling-off group; and n is 1 or 2.

In case of n=2, the coupler components formed by Q may be preferably of the same kind of couplers. The coupler components may also have conventional ballast groups.

The 5-pyrazolone coupler completed by Q can be derived as desired from among the known 5-pyrazolone couplers known in this field of art. As such couplers, various compounds are known and described in representative patents as follows: U.S. Pat. Nos. 2,343,703; 2,369,489; 2,600,788; 2,908,573; 3,062,653; 3,152,896; and 3,519,429. Typical 5-pyrazolone coupler components may be represented by the formulae:

In the above formulae, each of $R_{10}$ and $R_{11}$ represents an alkyl group having 1 to 40 atoms or an aryl group having 6 to 40 carbon atoms, and these groups may further contain substituents such as alkyl, aryl, alkoxy, aryloxy, alkylthio, arylthio, hydroxy, halogen, cyano, alkocycarbonyl, aryloxycarbonyl, carboxyl, acyl, acyloxy, carbonamide, carbamoyl, alkylsulfonyl, arylsulfonyl, sulfonamide and sulfamoyl.

The phenol coupler completed by Q can be derived as desired from among the phenol couplers known in this filed of art. As such couplers, are known various compounds, as disclosed in representative patents as follows: U.S. Pat. Nos. 2,367,531; 2,423,730; 2,772,162; 2,895,826 and 4,333,999.

Typical phenol coupler components may be represented by the following formulae:

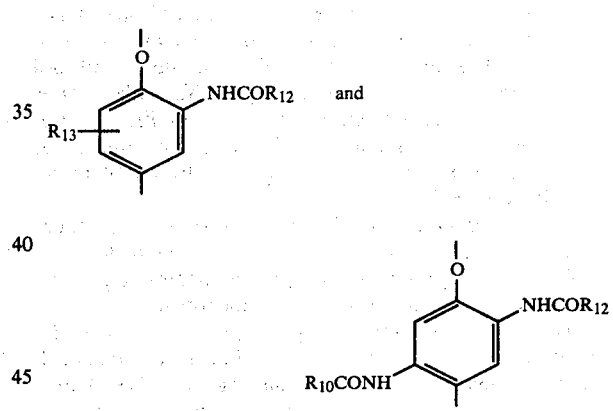

In the above formulae, $R_{10}$ is the same as defined above, $R_{12}$ is $R_{10}$ or $-NHR_{10}$, and $R_{13}$ is one or more halogen atoms or an alkyl group or an alkoxy group having 1 to 10 carbon atoms.

The coupling-off group represented by $R_9$ in formula (VIII) may be any coupling-off group known in this field of art. Representative of the coupling-off groups are inclusive of halogen, alkoxy, aryloxy, heterocycloxy, sulfonyloxy, acyloxy, heterocyclyl, thiocyano, alkylthio, arylthio, heterocyclylthio, sulfonamide, phosphonyloxy and arylazo.

As apparently seen from the above description, the compound of this invention, while it is enhanced in reactivity with an oxidized product of a color forming developing agent, is also endowed with outflow property from the photographic element with its reaction product (namely cyan dye) being made alkali soluble. For this advantage, the compound of this invention is applicable for a wider range of uses than in the prior art to be very advantageous in designing of light-sensitive materials. For instance, although the amount of the prior art compounds to be used is naturally limited due to the color turbidity cased by the prior art compound so that the desired effect can not be obtained, the compound of this invention is free from such drawback and it can be used in as much an amount as necessary to obtain the desired effect. Also, as will readily be understood, when the coupler component contains a ballast group together with a water soluble group as in the 1-naphthol coupler disclosed in U.S. Pat. No. 2,979,405 and U.K. Pat. No. 975,939, the reaction product with an oxidized product of a color forming developing agent (namely cyan dye) remains in the photographic element and therefore the objects of this invention cannot be accomplished.

Specific exemplary compounds of this invention are shown below, but the compounds of this invention are not limited thereto.

(Exemplary compounds) Typical examples of the compounds represented by formula (I) where X is a TIME-PUG group:

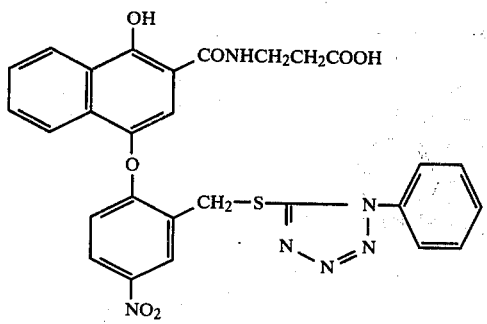

1

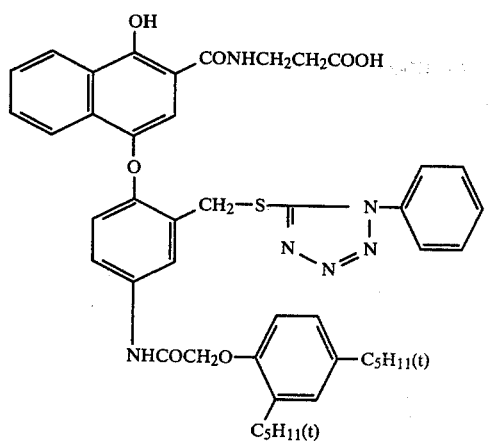

2

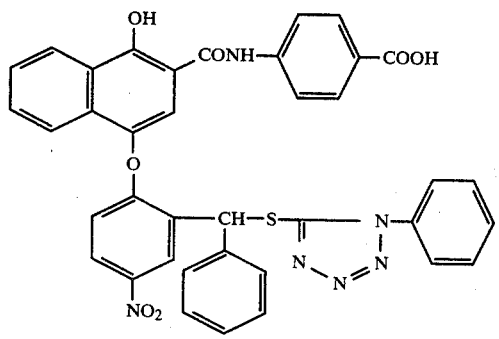

3

4
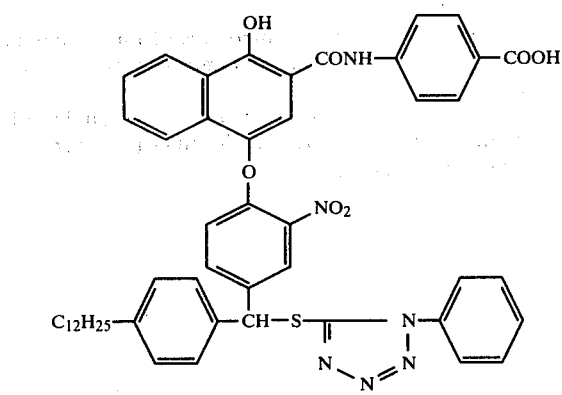
5
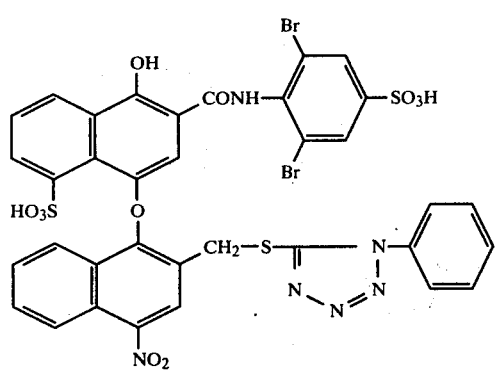
6
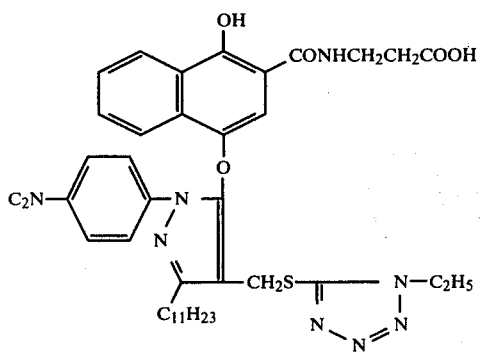
7
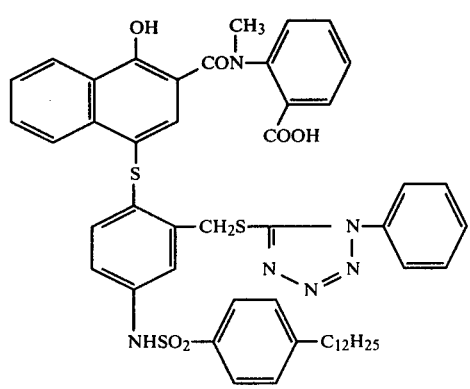

-continued
8
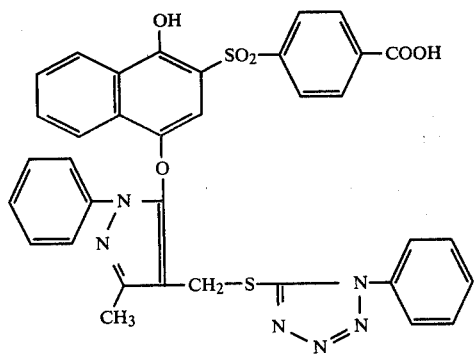
9
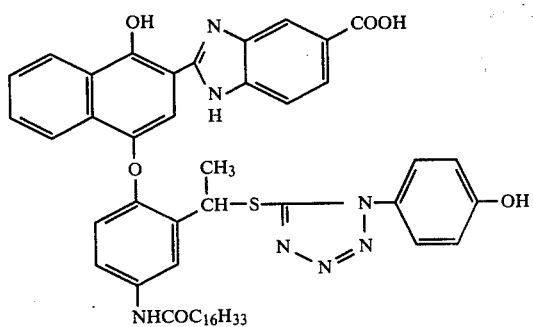
10
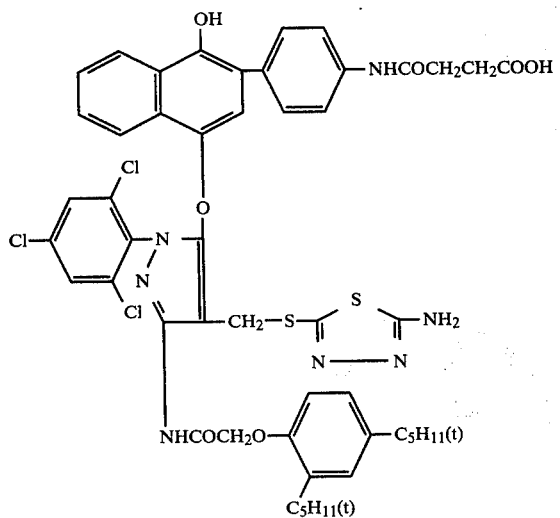
11
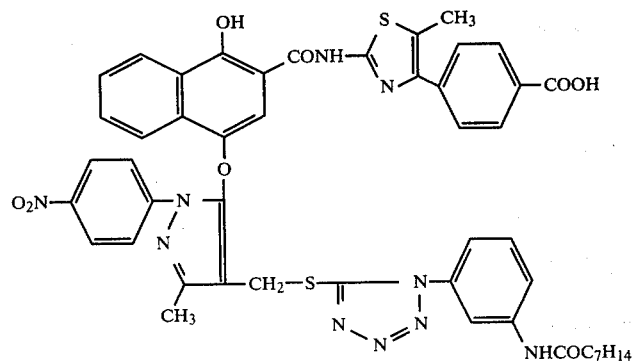

-continued
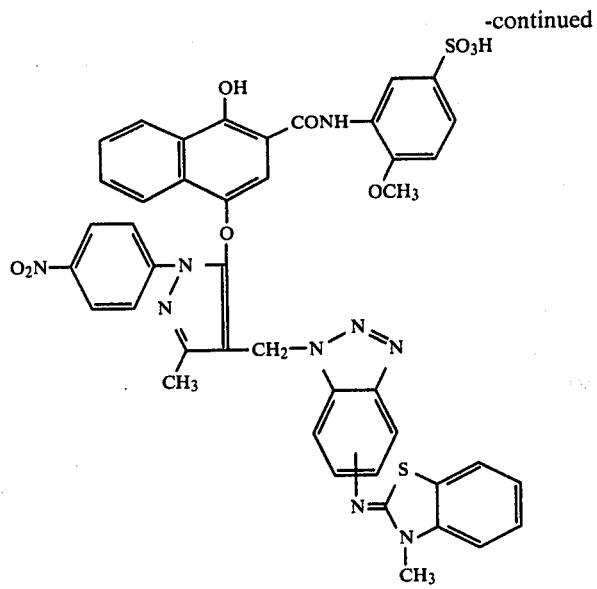
12
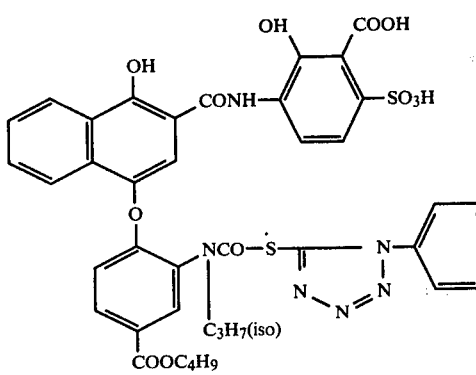
13
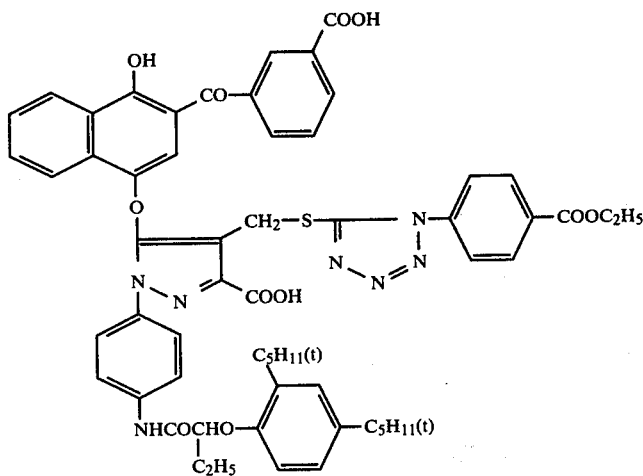
14
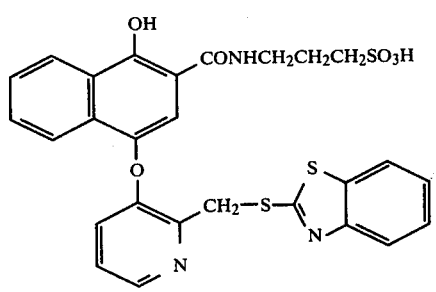
15

-continued
16
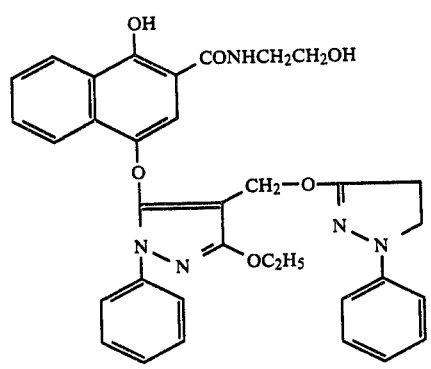
17
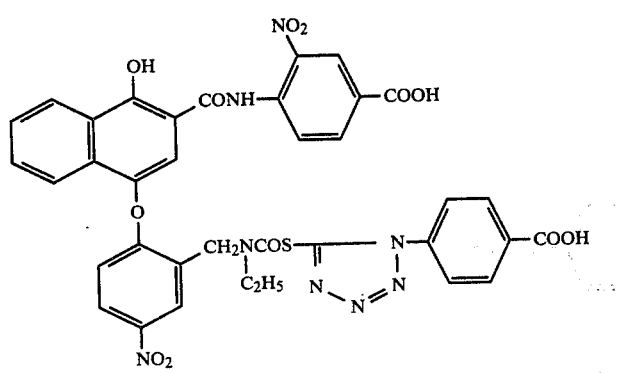
18
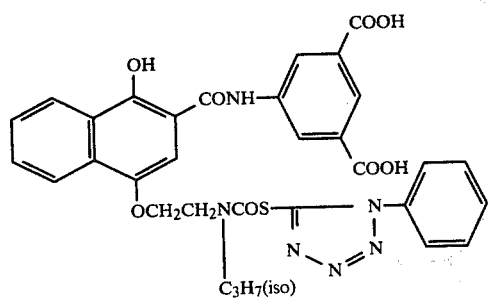
19
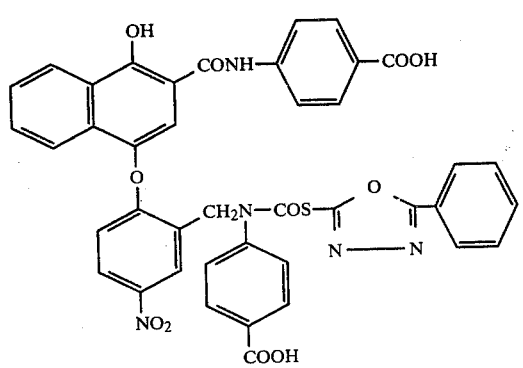

20
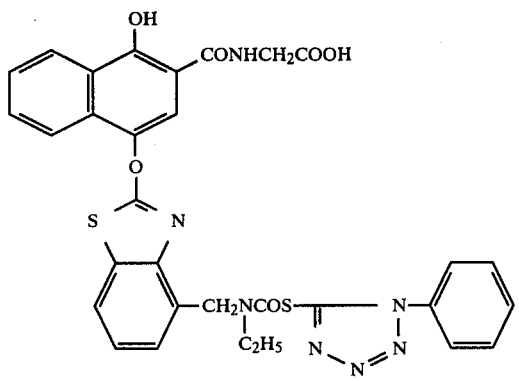
21
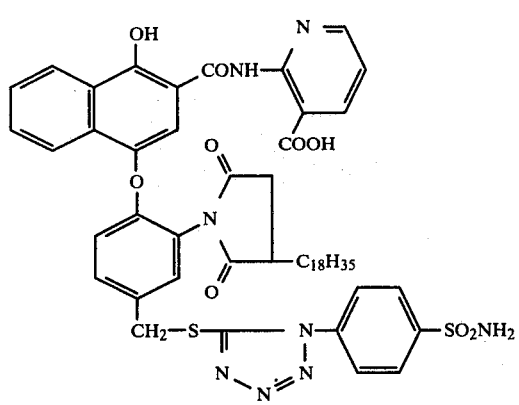
22
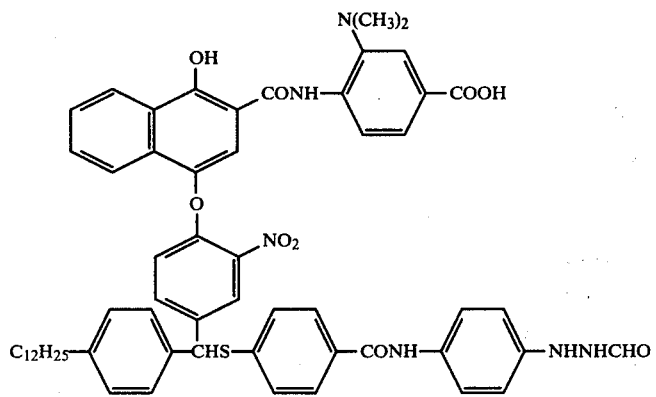
23
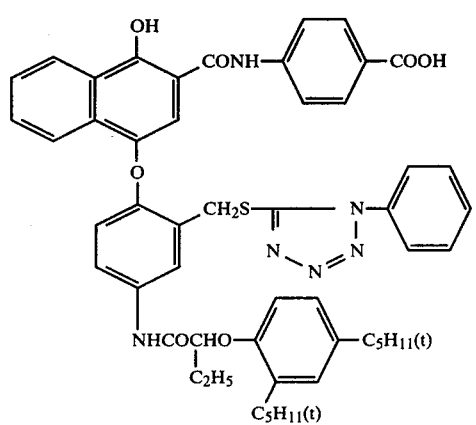

24
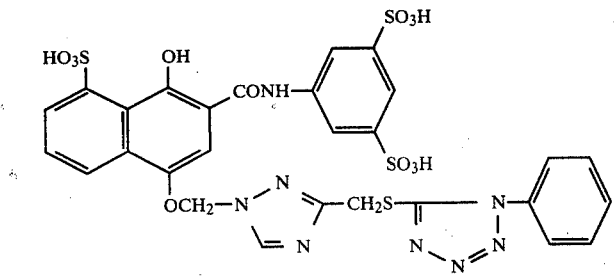
25
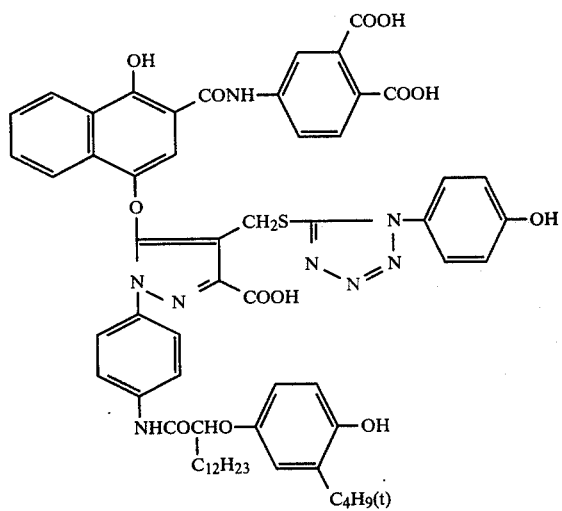
26
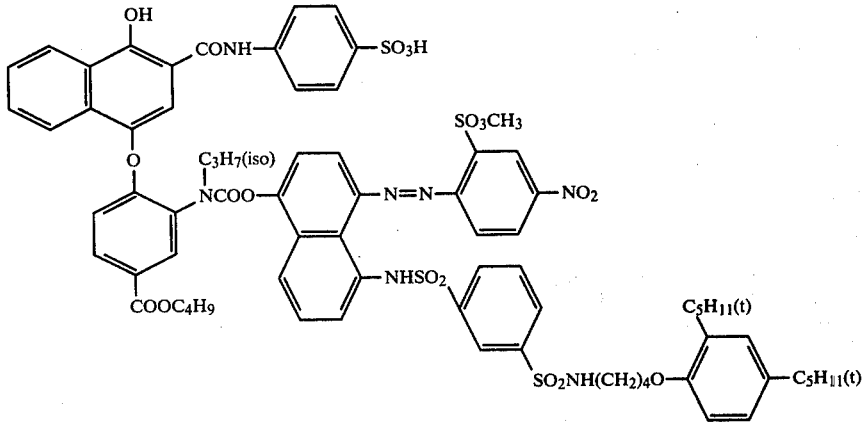
27
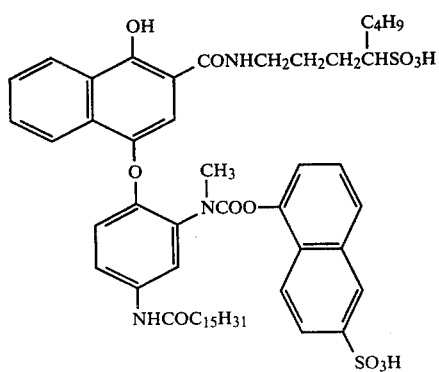

-continued
28
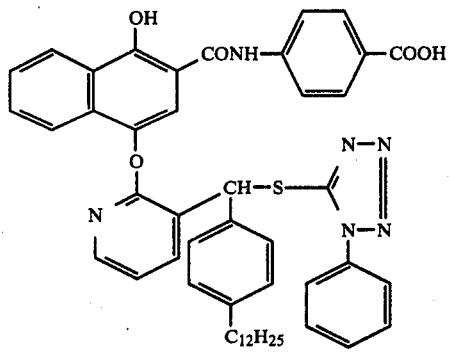
29
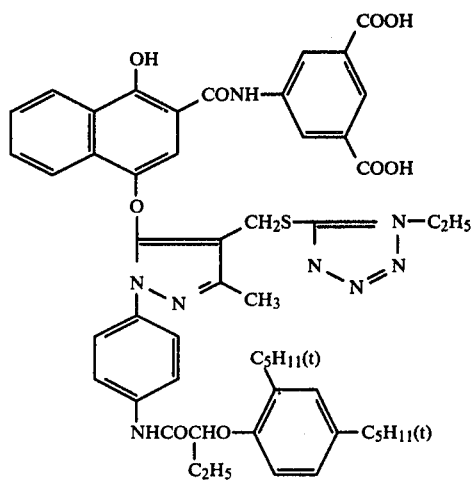
30
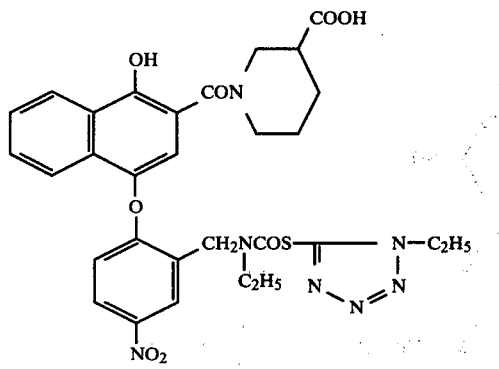
31
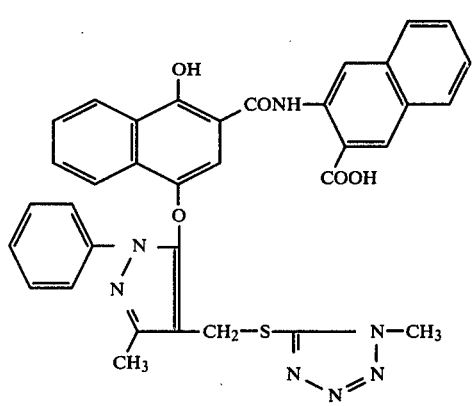

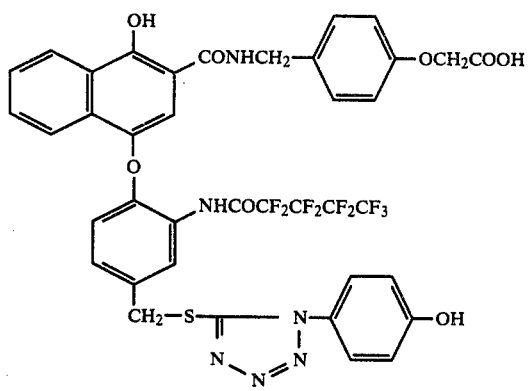
32
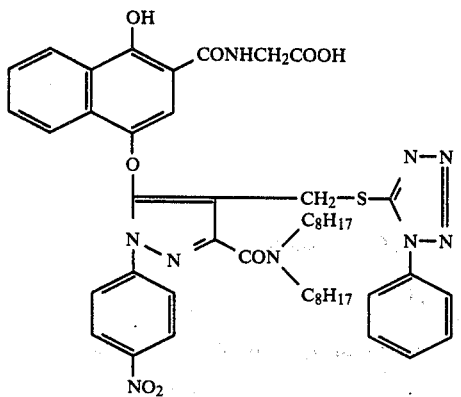
33
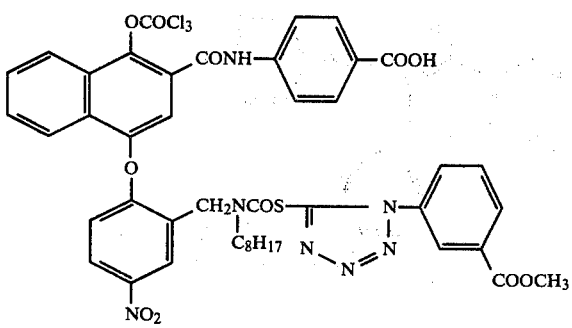
34
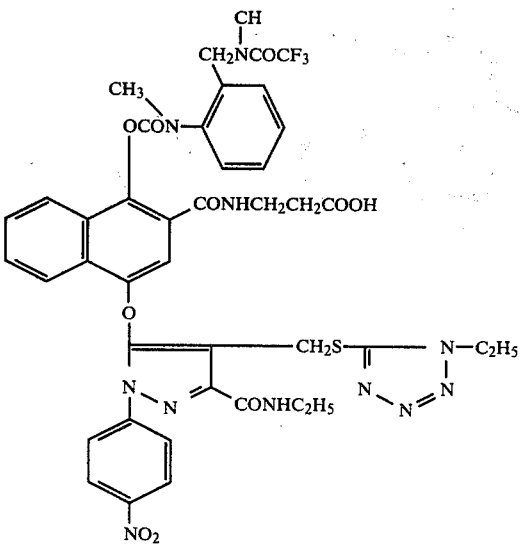
35

-continued
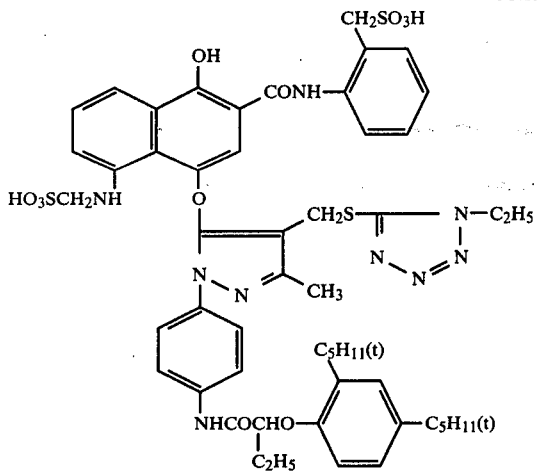
36
Typical examples of the compounds of the type capable of releasing development accelerators:
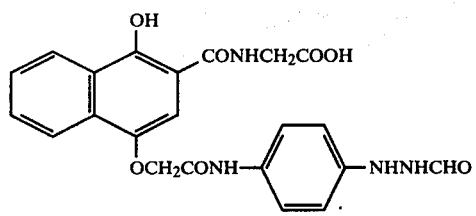
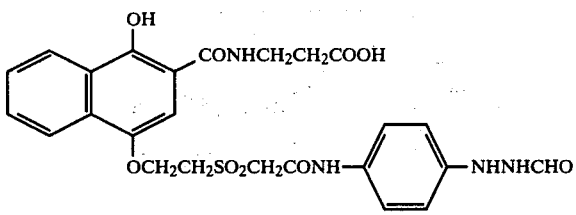
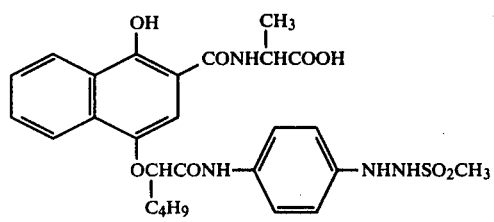
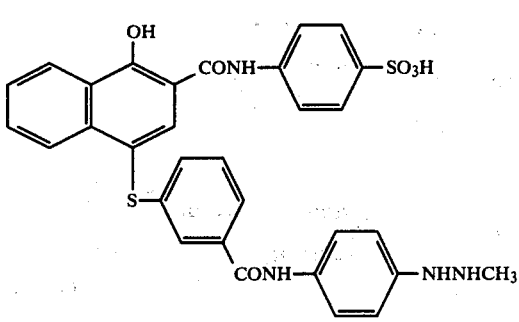
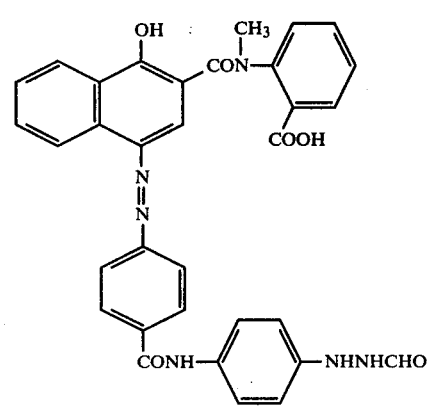
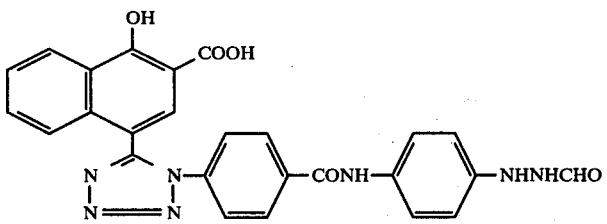

-continued
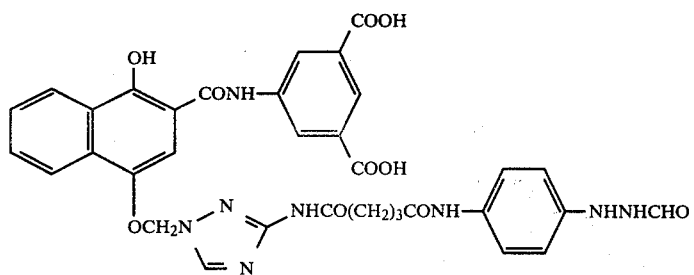
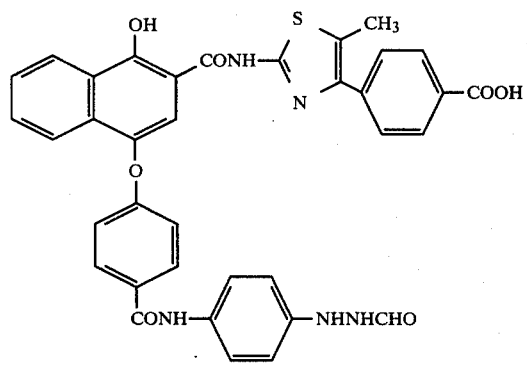
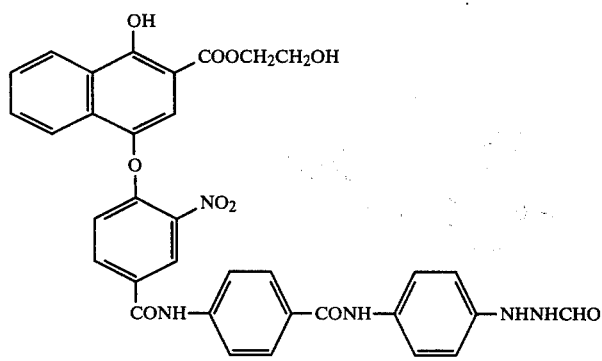
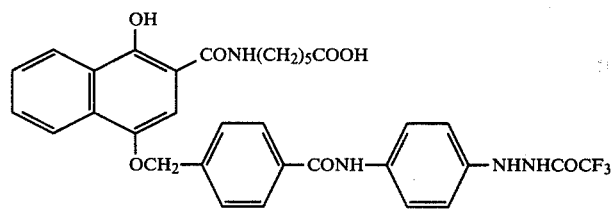
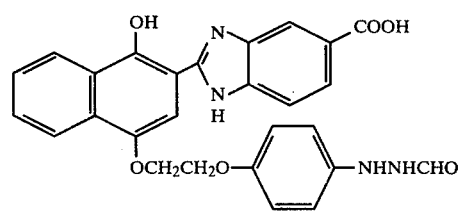
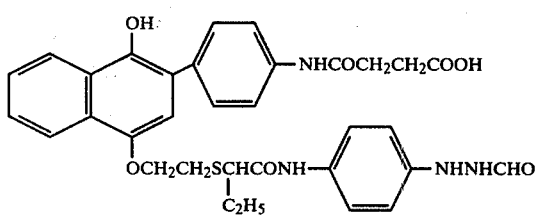

-continued
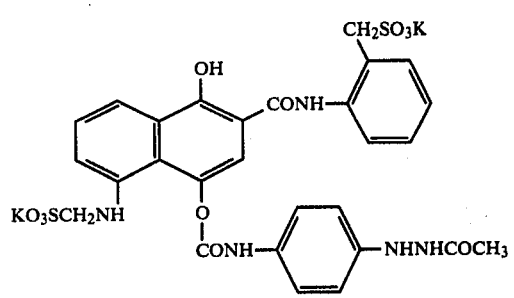
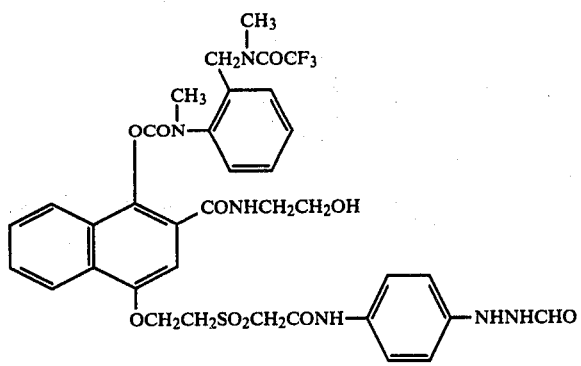
Typical examples of the compounds of the type capable of releasing couplers:
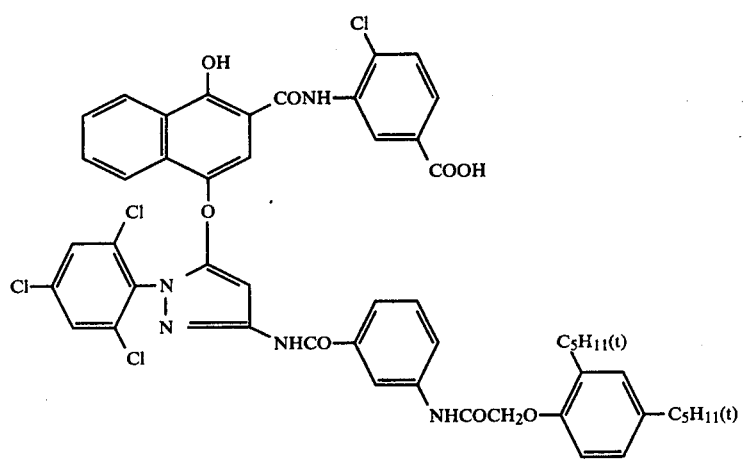
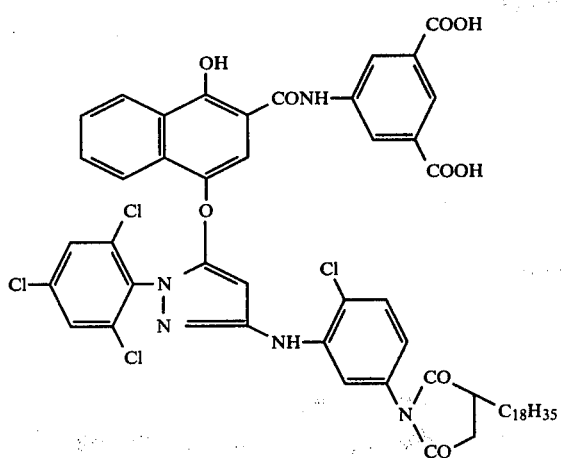

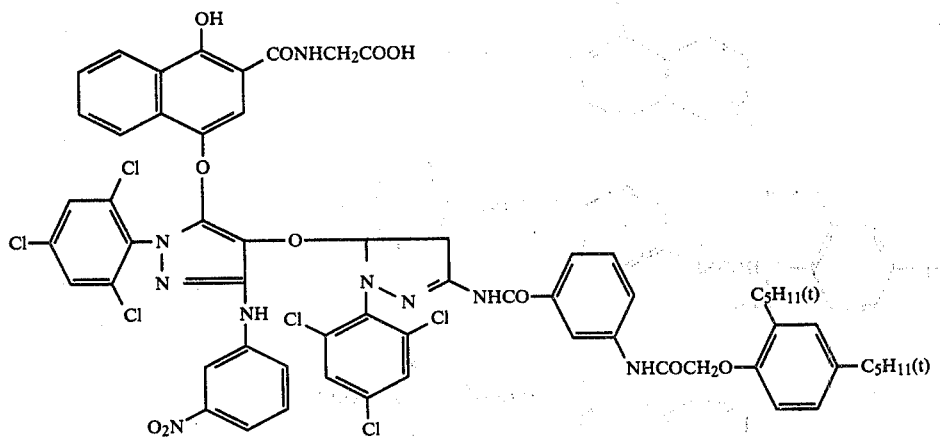
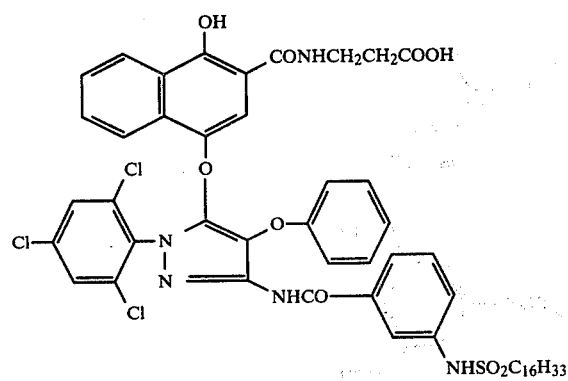
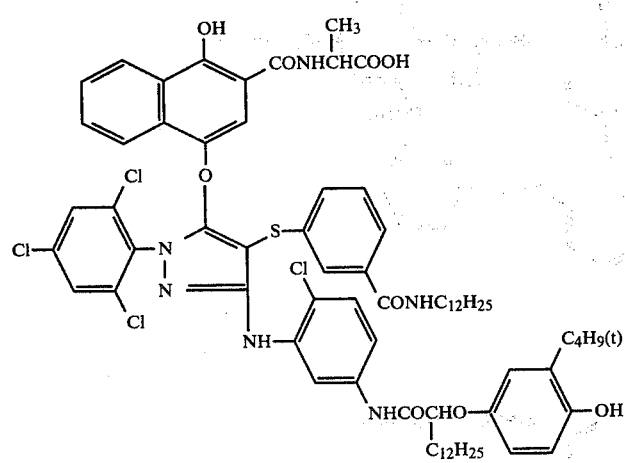
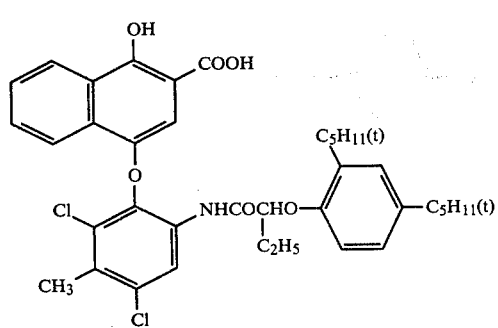

-continued
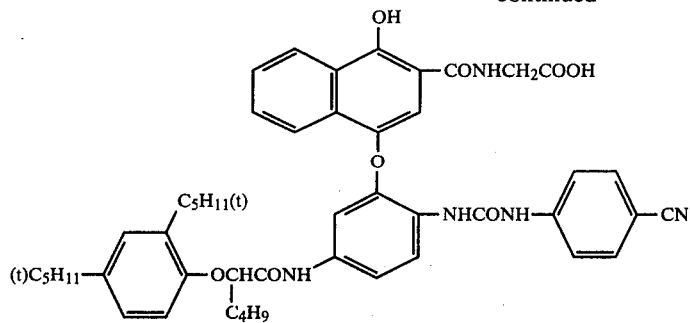
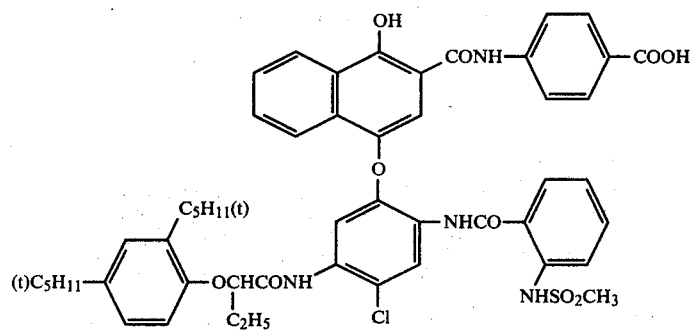
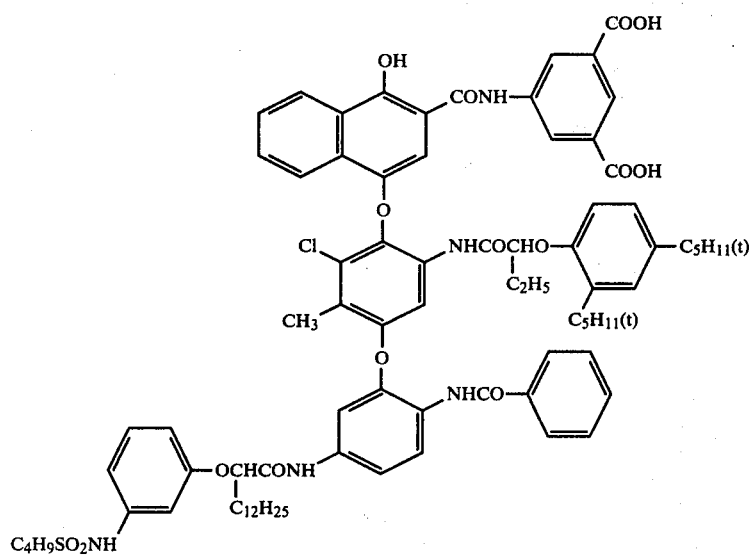
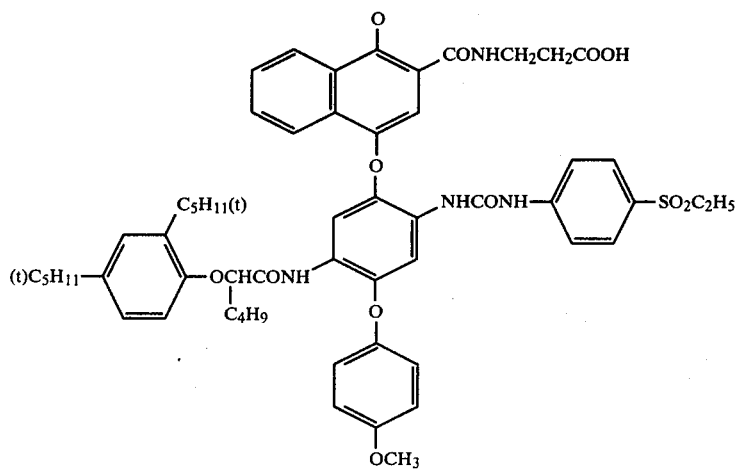

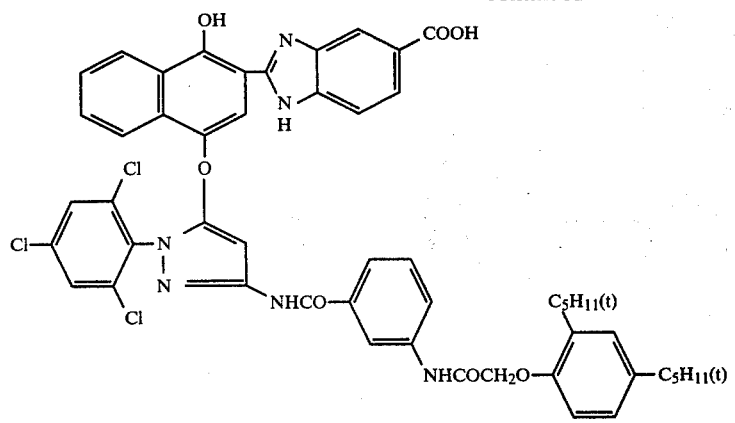
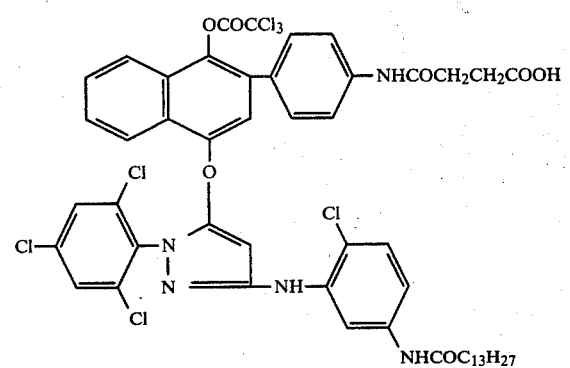
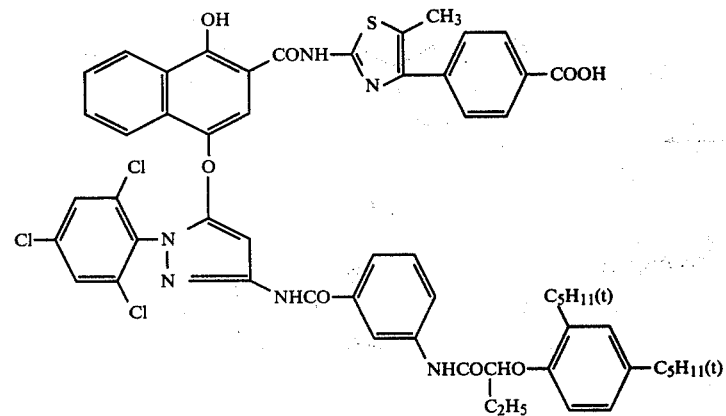
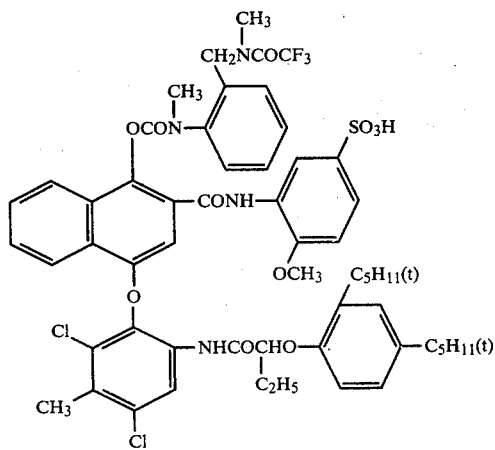

-continued
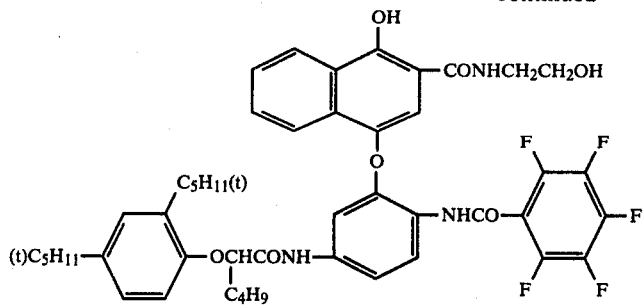
SYNTHESIS EXAMPLE 1
Synthesis of Exemplary compound No. 4
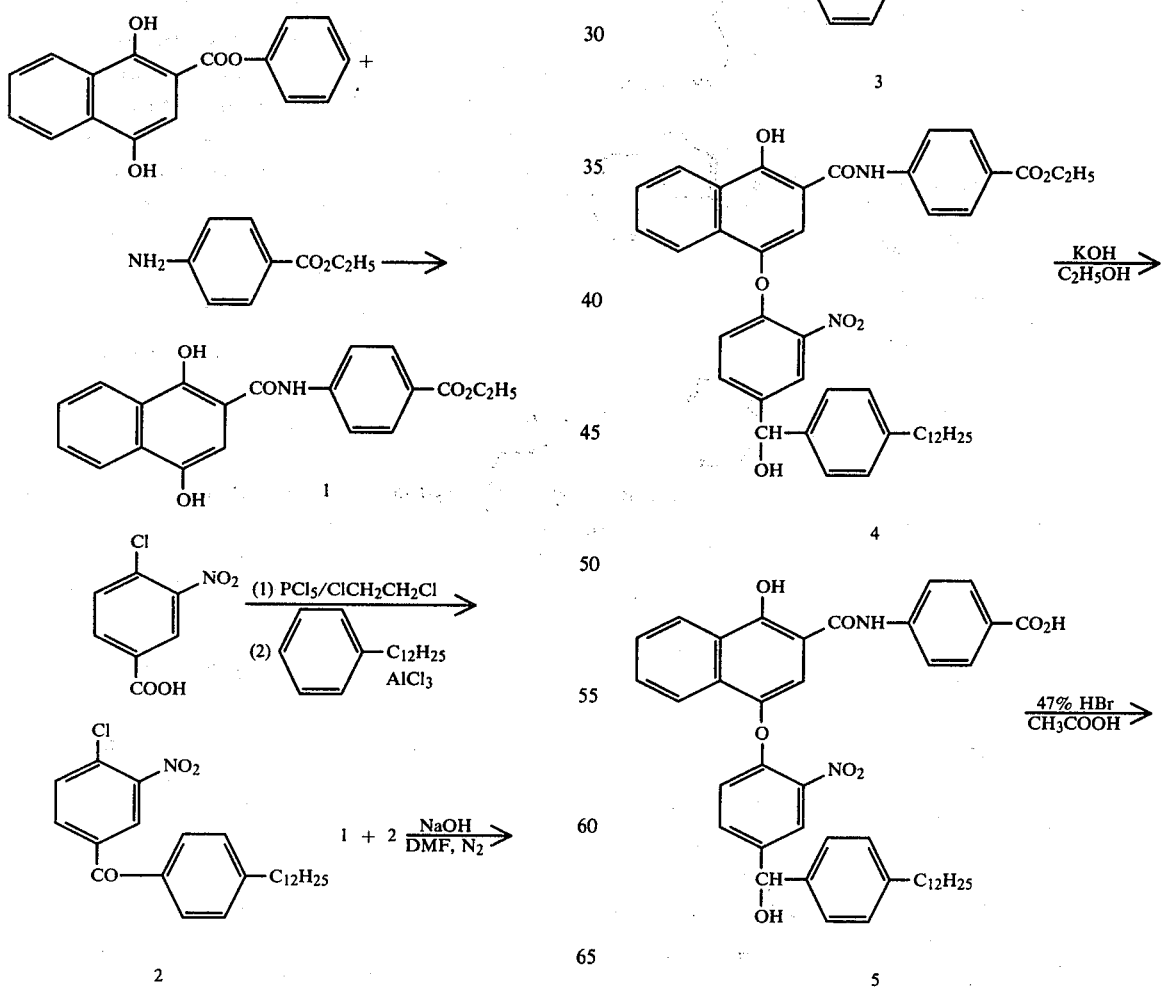
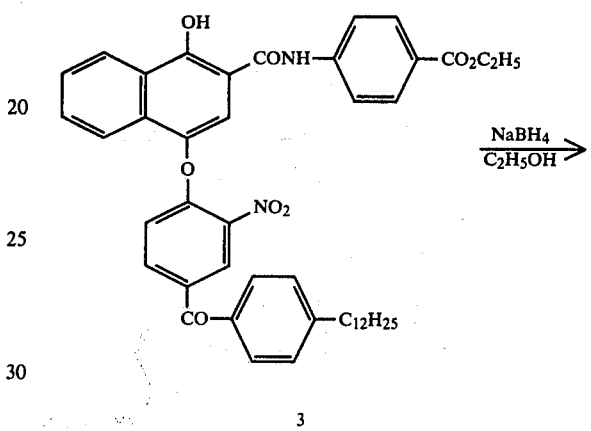

-continued

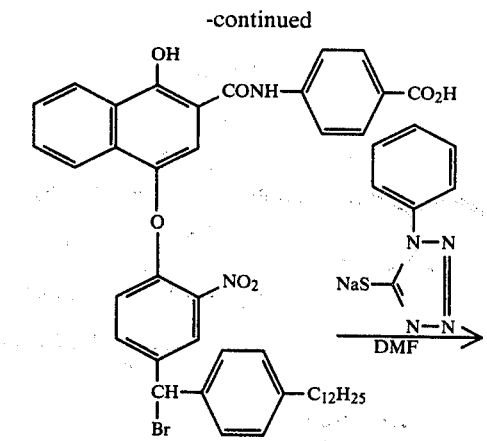

6

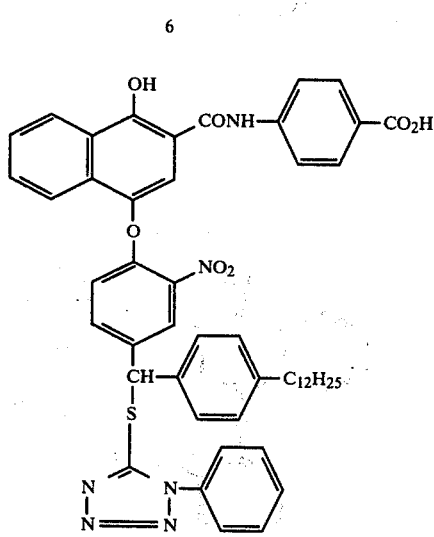

Exemplary Compd. No. 4

1. Synthesis of Compd. (1)

Into a 100 ml flask were charged 42.0 g of phenyl 1,4-dihydroxy-naphthoate and 24.7 g of ethyl para-aminobenzoate and the reaction was carried out at 150° to 160° C., while aspirating the inner atmosphere in the flask by an aspirator. The solid formed was crushed in $C_2H_5OH$ and filtered to obtain 22.5 g of Compd. (1) as a yellow solid.

2. Synthesis of Compd. (2)

To a suspension of 30.2 g of 4-chloro-3-nitrobenzoic acid in 50 ml of 1,2-dichloroethane was gradually added 34.5 g of phosphorus pentachloride. After refluxed for 2 hours, the reaction mixture was cooled to room temperature, at which 37.0 g of dodecyl benzene was added to the mixture. After 30.2 g of aluminum chloride was gradually added to the resultant mixture, reflux was conducted for 2 hours. The reaction mixture was poured into 500 ml of ice-water, chloroform was added thereto and the organic layer was extracted. The organic layer was washed first with a dilute hydrochloric acid solution, then with a sodium hydroxide solution, followed by concentration, to give 58.5 g of Compd. (2) as a dark brown liquid.

3. Synthesis of Compd. (3)

Into a solution of 22.5 g of Compd. (1) and 34.3 g of Compd. (2) dissolved in 200 ml of dimethylformamide, there was added a solution of 5.3 g of sodium hydroxide dissolved in 15 ml of water, while passing nitrogen into the reaction vessel, and the reaction was carried out 30 minutes. When the reaction mixture was thrown into one liter of ice-water containing 10 ml of a 35% hydrochloric acid, there was formed a solid. The solid was filtered and recrystallized from benzene-hexane to obtain 29.2 g of Compd (3).

4. Synthesis of Compd. (4)

Into a suspension of 25 g of Compd. (3) in 100 ml of ethyl alcohol was gradually added 1.5 g of sodium borohydroxide, followed by stirring for 30 minutes. The reaction mixture was thrown into 500 ml of ice-water containing 10 ml of a 36% hydrochloric acid, whereby a solid was precipitated. The solid was collected by filtration, washed with water and dried to obtain 25 g of Compd. (4).

Synthesis of Compd. (5)

To a solution of 25 g of Compd. (4) dissolved in 100 ml of ethyl alcohol was added a solution of 11 g of potassium hydroxide dissolved in 20 ml of water. After the mixture was stirred for 5 hours, the reaction mixture was thrown into 500 ml of ice-water containing 10 ml of a 36% hydrochloric acid. The solid precipitated was collected by filtration, washed with water and dried to obtain 22.5 g of Compd. (5).

6. Synthesis of Compd (6)

To 22.5 g of Compd. (5) was added 200 ml of acetic acid, and the mixture was heated at 70° C. to prepare a solution. Into the resultant solution was gradually added dropwise a mixture of 13.4 g of a 47% hydrobromic acid and 15 ml of acetic acid. Stirring was continued at 75° C. for 2 hours. The solid precipitated during the reaction was collected by filtration, thoroughly washed with acetic acid, then with hexane and dried to obtain 20.3 g of Compd. (6).

7. Synthesis of Exemplary compound No. 4

A solution of 20.3 g of Compd. (6) and 5.2 g of sodium salt of 1-phenyl-5-mercaptotetrazole dissolved in 100 ml of dimethylformamide was refluxed for one hour and then the reaction mixture was poured into 500 ml of ice-water. The resultant solid was collected by filtration, washed with water and dried. The dried product was recrystallized from ethyl acetate-hexane to obtain 23 g of Exemplary compound No. 4. m.p.: 176°–178° C. (decompd.). This product was identified as Exemplary compound No. 4 from elemental analysis, NMR and Field Description-Mass (FD-Mass).

SYNTHESIS EXAMPLE 2
Synthesis of Exemplary Compound No. 23
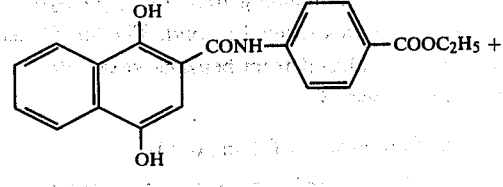
1
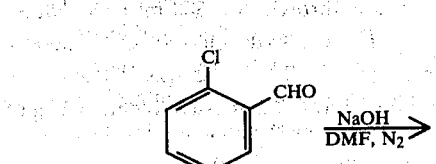
2
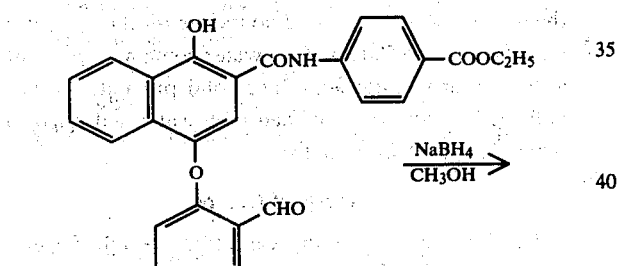
3
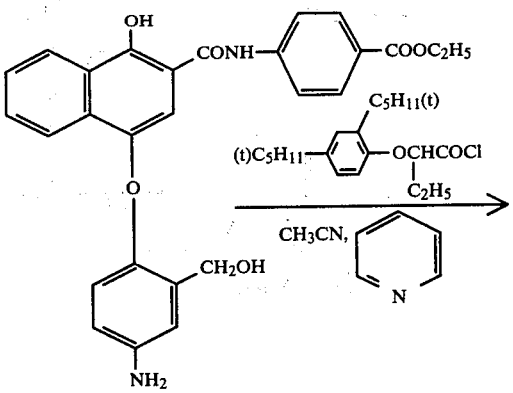
4
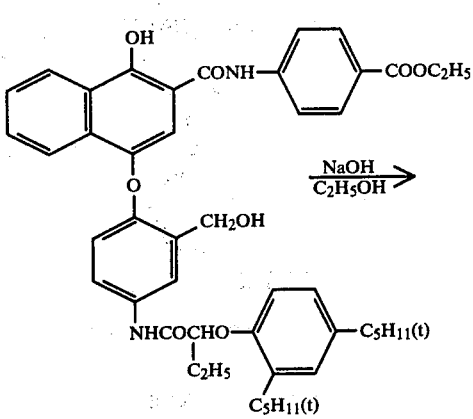
5
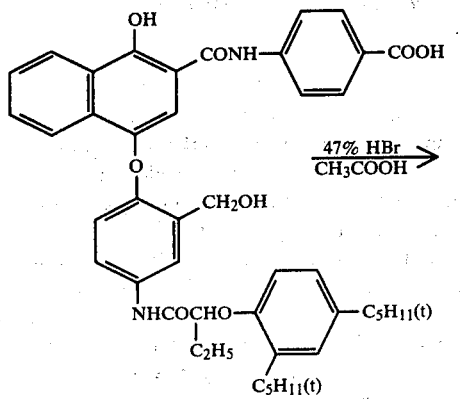
6

-continued

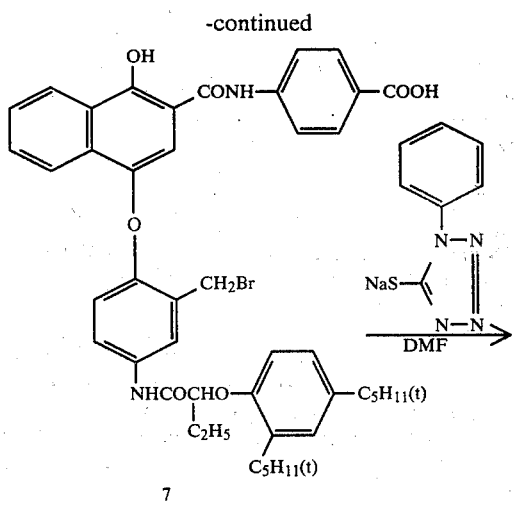

7

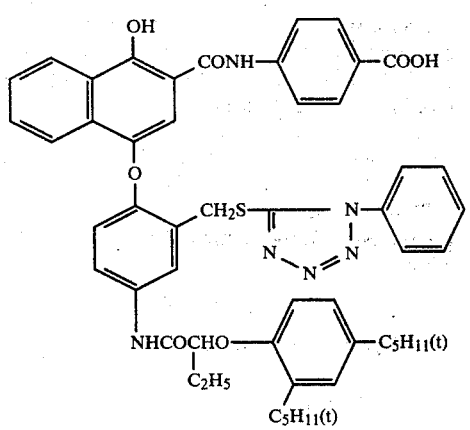

Exemplary Compd. No. 23

1. Synthesis of Compd. (2)

Into a solution of 36 g of Compd. (1) and 19 g of 2-chloro-5-nitrobenzaldehyde dissolved in 300 ml of dimethylformamide, there was added a solution of 8.2 g of sodium hydroxide in 40 ml of water, while passing nitrogen into the reaction vessel, and the reaction was carried out at room temperature for 1 hour. The reaction mixture was thrown into 2 liters of ice-water containing 20 ml of a 36% hydrochloric acid, whereby a solid was formed. The solid was filtered and washed with water. The product was boiled in 300 ml of ethyl acetate, cooled and collected by filtration to obtain 39 g of Compd. (2).

2. Synthesis of Compd. (3)

To a suspension of 39 g of Compd. (2) in 400 ml of methanol was added gradually 7.4 g of sodium borohydride, followed by stirring for 30 minutes. The reaction mixture was thrown into 1.5 liter of ice-water containing 30 ml of a 36% hydrochloric acid, whereby a solid was formed. The solid was filtered and washed with water. The product was boiled in a solvent mixture of 400 ml of methanol and 100 ml of acetone, cooled and collected by filtration to obtain 36 g of Compd. (3).

3. Synthesis of Compd. (4)

A mixture of 15 g of Compd. (3), 400 ml of ethyl acetate, 200 ml of acetic acid and 40 ml of water was boiled under stirring, and 16 g of a reduced iron was added to the mixture, followed by stirring for 30 minutes. The reaction mixture, while it was hot, was subjected to suction filtration and the residue was washed with 100 ml of ethyl acetate. The resultant reaction mixture was neutralized with sodium hydrogen carbonate, and then the ethyl acetate solution was dried on sodium sulfate. After evaporation of ethyl acetate under reduced pressure, the resultant oily product was mixed with 50 ml of benzene and heated, whereby crystallization occured. The crystals were collected by filtration and recrystallized from 100 ml of ethyl acetate to obtain 6.7 g of Compd. (4).

4. Synthesis of Compd. (5)

To a mixture of 6.7 g of Compd. (4), 1.13 g of pyridine and 300 ml of acetonitrile was added 4.9 g of 2-(2,4-ditert-amylphenoxy)-butyryl chloride, and the resultant mixture was boiled under stirring for one hour. The reaction mixture was thrown into 1.5 liters of ice-water and the solid precipitated was filtered, washed with water and dried. The product was recrystallized from a solvent mixture of 20 ml of methanol and 20 ml of ethyl acetate to obtain 7.4 g of Compd. (5).

5. Synthesis of Compd. (6)

To a mixture of 6 g of (5) and 100 ml of ethanol was added 1.6 g of sodium hydroxide, followed by boiling under stirring for one hour. The reaction mixture was thrown into 500 ml of ice-water containing 10 ml of a 36% hydrochloric acid and the solid precipitated was filtered, washed with water and dried. The product was recrystallized from 30 ml of ethyl acetate to obtain 5.5 g of Compd. (6).

6. Synthesis of Compd. (7)

A mixture of 5.5 g of Compd. (6) and 80 ml of acetic acid was heated to 70° C., and 3.9 ml of a 47% hydrobromic acid was added dropwise thereto over 15 minutes. Then, stirring was conducted under heating at 70° C. for one hour, the resultant mixture was thrown into 500 ml of ice-water and the solid precipitated was filtered, washed with water and dried. The product was recrystallized from 100 ml of ethyl acetate to obtain 4.9 g of Compd. (7).

7. Synthesis of Exemplary compound No. 23

A solution of 3.5 g of Compd. (7) and 1.6 g of sodium salt of 1-phenyl-5-mercaptotetrazole dissolved in 30 ml of dimethylformamide was heated on a hot water bath for 8 hours. The reaction mixture was thrown into 200 ml of ice-water, and the solid precipitated was filtered, washed with water and dried. The product was recrystallized from 40 ml of ethyl acetate to obtain 3.1 g of Exemplary compound No. 23. m.p. 215°–218° C. (decompd.)

This product was identified as Exemplary compound No. 23 from elemental analysis, NMR and FD-Mass.

SYNTHESIS EXAMPLE 3

Synthesis of Exemplary compound No. 37

Exemplary Compd. No. 37

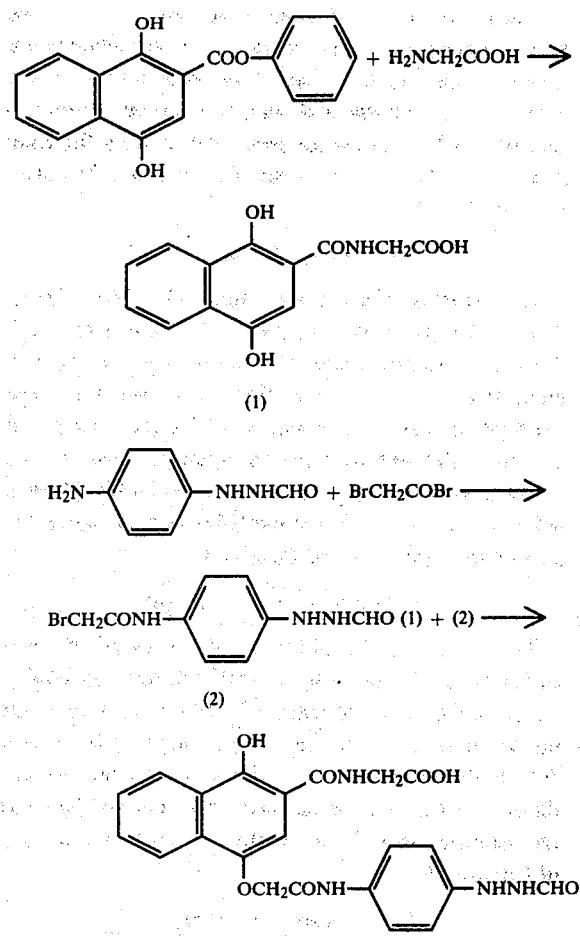

1. Synthesis of Compd. (1)

A suspension of 210 g of phenyl 1,4-dihydroxy-2-naphthoate in 800 ml of ethanol was stirred under a nitrogen atmosphere. To the suspension was added a solution prepared from 67 g of glycine, 35.7 g of sodium hydroxide and 200 ml of water, and the mixture was refluxed under heating for 4 hours. After cooling, the reaction mixture was dissolved in 3 liters of water and the resultant solution was extracted with ethyl acetate, followed by removal of the organic layer. The aqueous layer was made acidic with hydrochloric acid, and the precipitate was collected by filtration and washed with water. After drying, recrystallization from ethyl acetate gave 94 g of Compd. (1).

2. Synthesis of Compd. (2)

A solution of 15.1 g of 1-formyl-2-(4-aminophenyl)-hydrazide which had been synthesized according to the method disclosed in Japanese Provisional Patent Publication No. 74729/1979 dissolved in 200 ml of tetrahydrofuran was stirred under cooling on an ice-water bath. After 10.1 g of triethylamine was added to the mixture, 21.0 g of bromoacetyl bromide was added dropwise thereto while controlling the temperature at not over 5° C. After the dropwise addition, the mixture was stirred for 3 hours and the resultant triethylamine hydrochloride was removed by filtration. The filtrate was evaporated under reduced pressure, and the residue was dissolved under heating in methanol and the solution was left to stand, whereby crystals were precipitated. The crystals were collected by filtration and dried to obtain 21.3 g of Compd. (2).

3. Synthesis of Exemplary compound No. 37

To a solution of 5.2 g of Compd. (1) dissolved in 100 ml of a dried and degasified dimethyl sulfoxide (DMSO), there was added 1.92 g of a 50% sodium hydride in an nitrogen atmosphere at room temperature. The mixture was stirred at 60° C. until foaming ceased. Then, the reaction mixture was cooled to room temperature, and a solution of 5.4 g of Compd. (2) dissolved in 40 ml of dry dimethylformamide (DMF) was added dropwise thereinto over 15 minutes. After one hour, the mixture was poured into an ice-water containing acetic acid, and extracted with ethyl acetate. After washing with water and drying, the ethyl acetate was evaporated and the residue was chromatographed on a column with silica gel (eluant: ethyl acetate/methanol=4/1). The desired fractions were recovered, stripped of the solvent by evaporation and recrystallized from methanol to obtain 1.9 g of Exemplary compound No. 37. m.p. 154°-156° C.

This product was identified to be Exemplary compound No. 37 by elemental analysis, NMR and FD-Mass.

SYNTHESIS EXAMPLE 4

Synthesis of Exemplary compound No. 57

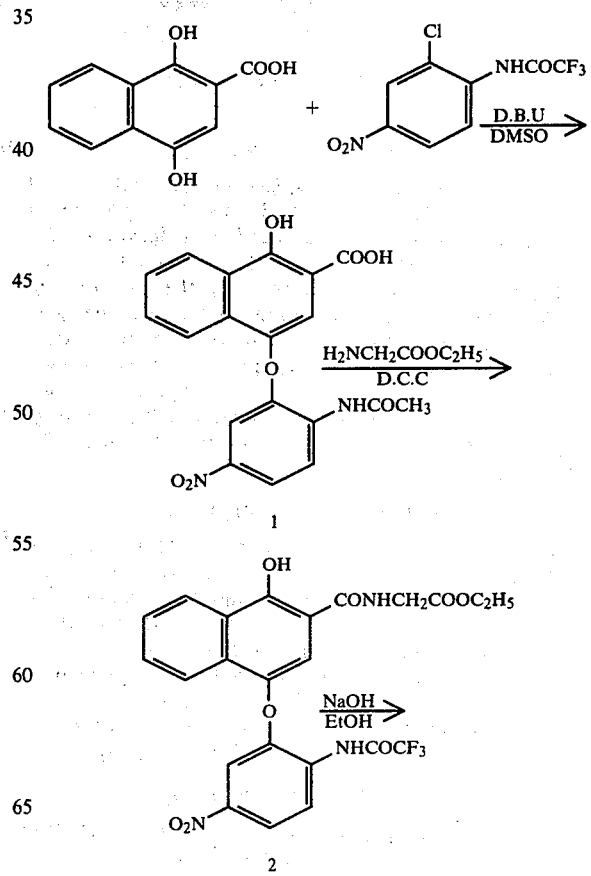

-continued

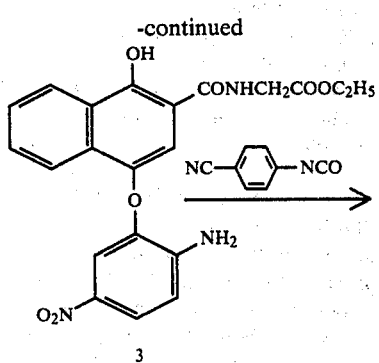

3

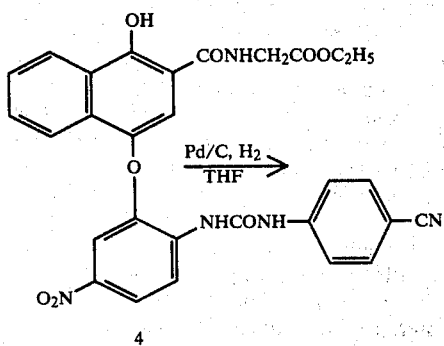

4

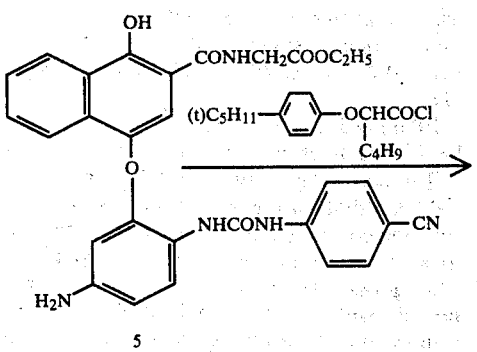

5

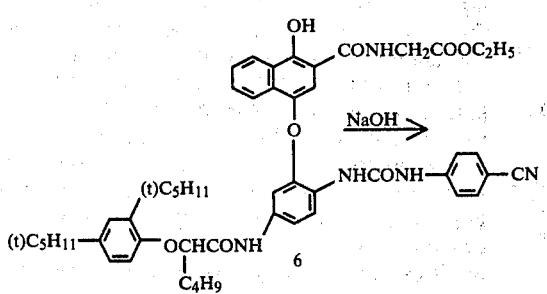

6

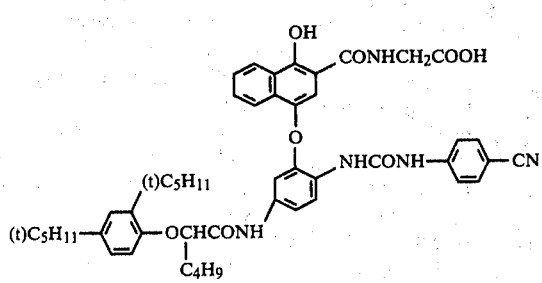

Exemplary Compd. No. 57

1. Synthesis of Compd. (1)

In 500 ml of dimethyl sulfoxide were dissolved 20.4 g of 1,4-dihydroxy-2-naphthoic acid, and 26.9 g of 3-chloro-4-trifluoroacetamido-nitrobenzene and nitrogen gas was passed through the resultant solution. Into this solution, there was added 30.4 g of 1,8-diaza-bicyclo(5.4.0)undecene-7 over 15 minutes. After the addition, stirring was conducted at 40° C. for one hour and the reaction mixture was poured into 2 liters of ice-water containing 20 ml of a 36% hydrochloric acid. The precipitates were collected by filtration and washed with water. This product is suspended in 200 ml of methanol, boiled for 10 minutes, cooled and thereafter filtered to give 27.1 g of Compd. (1).

2. Synthesis of Compd. (2)

In 300 ml of dioxane were dissolved 21.8 g of Compd. (1) and 5.2 g of glycine ethyl ester. To this solution was added a dioxane solution having 10.3 g of dicyclohexylcarbodiimide dissolved therein, while controlling the inner temperature at not over 15° C. After the addition, stirring was continued at room temperature for 4 hours, and the urea formes was separated by filtration. Evaporation of dioxane under reduced pressure gave crystals, which were then recrystallized from ethyl acetate to obtain 18.5 g of Compd. (2).

3. Synthesis of Compd. (3)

To a suspension of 18 g of Compd. (2) in 200 ml of ethanol was added 25 ml of an aqueous 5N sodium hydroxide, followed by stirring at room temperature for 30 minutes. To the reaction mixture was added 10 ml of acetic acid, and the mixture was extracted with ethyl acetate. After washing with water, the extract was dried over magnesium sulfate, and then the ethyl acetate was evaporated under reduced pressure to obtain Compd. (3). This product was used as such without purification in the subsequent step.

4. Synthesis of Compd. (4)

Compd. (3) synthesized in the preceding step was dissolved in 200 ml of acetonitrile and 5 g of p-cyanophenyl isocyanate was added to the resultant solution, followed by boiling under stirring for 5 hours. After evaporation of the acetonitrile under reduced pressure, methanol was added to the residue and the mixture was heated, whereby crystallization occurred. The crystals were collected by filtration and recrystzilized from a solvent mixture of ethanol/acetone (2/1) to obtain 10.8 g of Compd. (4).

5. Synthesis of Compd. (5)

To a solution of 10.5 g of Compd. (4) dissolved in 200 ml of tetrahydrofuran was added 1.0 g of 5% palladium-carbon catalyst, and catalytic reduction was carried out at normal pressure. On reaction of a theoretical amount of hydrogen, the catalyst was separated by filtration and the tetrahydrofuran solution was used as such in the subsequent step.

6. Synthesis of Compd. (6)

To the above tetrahydrofuran solution was added 1.46 g of pyridine, and 6.8 g of α-(2,4-di-tert-amyl-phenoxy)hexanoyl chloride was added to the resultant solution. After stirring at room temperature for 2 hours, the pyridine hydrochloride was filtered off and the tetrahydrofuran was evaporated under reduced pressure. The residue was chromatographed on a column with silica gel using a n-hexane-ethyl acetate solvent mixture (mixing ratio=2:1) as eluant to obtain 4.4 g of Compd. (6).

7. Synthesis of Exemplary compound No. 57

To a suspension of 4.0 g of Compd. (6) in 50 ml of ethanol was added 3 ml of an aqueous 5N sodium hydroxide, and the mixture was boiled under stirring for 30 minutes. The reaction mixture was poured into 200 ml of ice-water containing 5 ml of a 36% hydrochloric acid, and the white precipitates were collected by filtration, washed with water and dried. Recrystallization of the product from a 90% alcohol gave 2.8 g of Exemplary compound No. 57. m.p. 141°–143° C.

This product was identified to be Examplary compound No. 57 by elemental analysis, NMR and FD-Mass.

The compounds according to this invention can be used in light-sensitive silver halide color photographic materials in various modes depending on the kind of X in the above formula (I), and the same methods applied in the prior art may also be applicable for the compounds according to this invention.

The compounds of this invention, as apparently seen from the foregoing description, are highly reactive couplers and at the same time have the great specific feature of being excellent in alkali flow-out property without remaining in a photographic element. Due to such a specific feature, the compounds of this invention will provide a great variety and diversity of means to the researchers in this field of art as the techniques for making higher image quality of light-sensitive silver halide color photographic materials. That is, the researchers in this field of art can accomplish improvements to higher image quality without bothering about the problem of color turbidity at all and by having various photographic actions of the compounds of this invention exhibited to full extent.

A diversity of coupling-off groups leads to a diversity of photographic actions of the compounds of this invention, and when X is a development accelerator, higher sensitization (improvement of graininess) of minute particulate silver halide emulsion is made possible; when X is an image dye forming coupler, the coupler may be made multi-equivalent (improvement of graininess); or when X is a useful group through a timing group, control in time or distance of the photographic effects (improvements of graininess, sharpness and others) by photographically useful groups can be made possible. Therefore, it is preferred for the purpose of improvement of image quality to use various compounds of this invention in combination.

The compound of this invention can be used in combination with a colorless coupler or a colored coupler and added into a silver halide emulsion as the same emulsion together with a coupler, or alternatively as an independent emulsion into an auxiliary layer such as an intermediate layer, etc. The compound of this invention can be used either as a single species or as a combination of two or more species. In the above case when the compound of this invention is added into a silver halide emulsion layer, it may be added in an amount of 0.01 to 200 mol % per one mol of silver halide, preferably 0.05 to 50 mol %.

The compound according to this invention may be used in various kinds of light-sensitive silver halide photographic materials and useful for any of black-and-white, color and false color photographic materials, and also applicable for light-sensitive silver halide photographic materials in various uses such as black-and-white in general, black-and-white for printing, X-ray, electron beam, black-and-white for high resolution, color in general, color X-ray, diffusion transfer type color, etc.

When the compound of this invention is to be applied for a light-sensitive silver halide color photographic material, it can be used in combination with a known twoequivalent or fourequivalent coupler.

The light-sensitive material of this invention may have a layer constitution according to conventional subtractive color process. In principle, the basic layer constitution comprises three layers of a blue sensitive layer containing a yellow coupler for forming a yellow dye therein, a green sensitive layer containing a magenta coupler for forming a magenta dye therein and a red sensitive layer containing a cyan coupler for forming a cyan dye therein. Further any or all of these respective layers may be made into a double or triple multi-layer structure for improvement of various photographic characteristics of the light-sensitive material such as color forming characteristic, color reproducibility, color forming dye graininess, etc.

As the silver halide to be used in the light-sensitive material of this invention, there may be included any silver halide used in conventional light-sensitive silver halide photographic materials such as silver chloride, silver bromide, silver iodide, silver chlorobromide, silver iodobromide, silver chloroiodobromide, and the like.

Film hardening treatment of the above emulsion may be also practiced according to conventional procedures.

The above light-sensitive color photographic material according to this invention, after imagewise exposure and color developing processing, may be subjected to a bleaching processing in a conventional manner. This processing may be conducted either simultaneously with or separately from fixing. The processing solution may be made into a bleach-fixing bath by adding, if necessary, a fixing agent. As the bleaching agent, there may be employed various compounds, and various additives such as bleaching promoters.

This invention can be realized in various modes of light-sensitive color photographic materials. One of them is to treat a photographic material having a silver halide emulsion layer containing a diffusion resistant coupler on a support with an alkaline developing solution containing an aromatic primary amine type color developing agent, thereby permitting a water insoluble or diffusion resistant dye to be left in the emulsion layer. According to another mode, a light-sensitive photographic material having a silver halide emulsion layer in combination with a diffusion resistant coupler on a support is treated with an alkaline developing agent containing an aromatic primary amine type color developing agent to make it soluble in an aqueous medium, thereby forming a diffusible dye, which is in turn transferred onto an image receiving layer comprising another hydrophilic colloid. That is, this is the diffusion transfer color system.

The above light-sensitive material of this invention is inclusive of all kinds of color light-sensitive materials such as color negative films, color positive films, color inversion films, color papers, etc.

This invention is illustrated in further detail by referring to the following Examples, by which the embodiments of this invention are not limited at all.

EXAMPLE 1

On a cellulose triacetate film applied with a subbing coating was provided the following coating. As a yellow coupler, 20 g of the compound having the structure as shown below was dissolved in 20 ml of tricresyl phosphate and 60 ml of ethyl acetate, and the resultant solution was mixed with 200 ml of a 5% aqueous gelatin solution containing 20 ml of a 5% aqueous solution of Alkanol B (alkylnaphthalene sulfonate, produced by E. I. Du Pont de Nemours & Company). The mixture was emulsified in a colloid mill to obtain an emulsified product. This dispersion was added to 1 kg of a blue sensitive silver iodobromide emulsion (containing 6 mol % of silver iodide) and then incorporated with 40 ml of a 2% aqueous solution of 1,2-bis(vinylsulfonyl)ethane as a film hardener, followed by coating and drying. (amount of silver coated: 20 mg/dm$^2$, coupler mol/Ag mol=0.1). The thus prepared light-sensitive silver halide color photographic material is called as Sample 1.

In the emulsified dispersion used in Sample 1, Exemplary compounds Nos. 2 and 5 of this invention were added, respectively, and preparations made, coated and dried similarly as in Sample 1 to provide Samples 2 and 3, respectively.

In the emulsified dispersion used in Sample 1, the Comparative compounds (A), (B) and (C) shown below were added, respectively, and preparations made, coated and dried similarly as in Sample 1 to provide Samples 4, 5 and 6, respectively.

Yellow coupler: A compound disclosed in Japanese Patent Publication No. 44420/1981

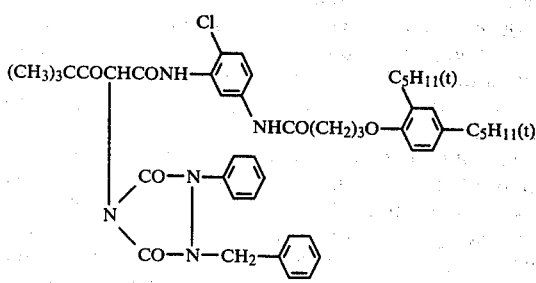

Comparative DIR coupler (A): A compound disclosed in U.S. Pat. No. 3,227,554

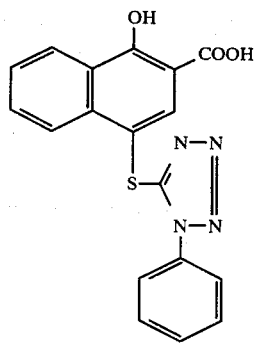

Comparative DIR coupler (B): A compound disclosed in U.S. Pat. No. 4,248,962

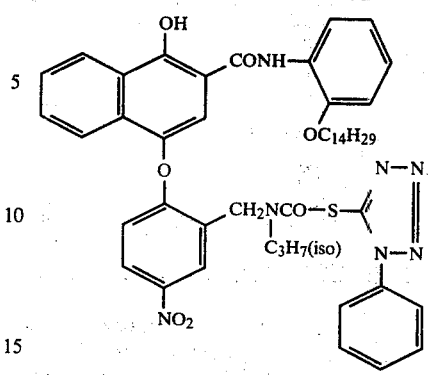

Comparative DIR coupler (C): A compound disclosed in Japanese Provisional Patent Publication No. 77635/1974

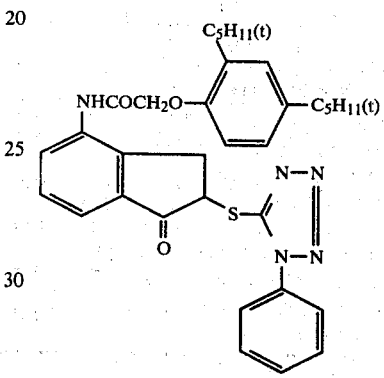

After each of these Samples was subjected to wedge exposure by an intensity scale sensitometer, color developing processing was applied thereon according to the following processing steps to obtain the results as shown in Table 1.

| [Processing steps] (38° C.) | Processing time |
|---|---|
| Color developing | 3 min. 15 sec. |
| Bleaching | 6 min. 30 sec. |
| Washing with water | 3 min. 15 sec. |
| Fixing | 6 min. 30 sec. |
| Washing with water | 3 min. 15 sec. |
| Stabilization | 1 min. 30 sec. |

The processing solutions employed in respective processing steps had the compositions shown below:

| [Composition of color developing solution] | |
|---|---|
| 4-Amino-3-methyl-N—ethyl-N—(β-hydroxyethyl)-aniline sulfate | 4.75 g |
| Anhydrous sodium sulfite | 4.25 g |
| Hydroxyamine.½ sulfate | 2.0 g |
| Anhydrous potassium carbonate | 37.5 g |
| Sodium bromide | 1.3 g |
| Nitrilotriacetic acid trisodium salt (monohydrate) | 2.5 g |
| Potassium hydroxide | 1.0 g |
| (made up to one liter with addition of water and adjusted to pH 10.0 with potassium hydroxide) | |
| [Composition of bleaching solution] | |
| Ferric ammonium ethylenediaminetetraacetate | 100.0 g |
| Diammonium ethylenediaminetetraacetate | 10.0 g |
| Ammonium bromide | 150.0 g |
| Glacial acetic acid | 10.0 ml |
| (made up to one liter with addition of water and | |

-continued

| | |
|---|---|
| adjusted to pH 6.0 with ammonia water) [Composition of fixing solution] | |
| Ammonium thiosulfate (50% aqueous solution) | 162 ml |
| Anhydrous sodium sulfite (made up to one liter with addition of water and adjusted to pH 6.5 with acetic acid) [Composition of stabilizing solution] | 12.4 g |
| Formalin (37% aqueous solution) | 5.0 ml |
| Konidax (trade name, produced by Konishiroku Photo Industry, Co., Ltd.) (made up to one liter with addition of water) | 7.5 ml |

In Table 1, the sensitivity values were represented as relative values to the sensitivity of Sample 1 as 100, and the turbidity values were given in terms of the percentage values of the Red densities when giving the Blue density of 1.0.

TABLE 1

| Sample No. | Compound | DIR amount added (mol/100 Ag mols) | S | γ | Fog | Color turbidity (%) |
|---|---|---|---|---|---|---|
| 1 | Control | — | 100 | 2.05 | 0.15 | 5 |
| 2 | Exemplary Compd. No. 2 | 0.3 | 85 | 0.80 | 0.08 | 5 |
| 3 | Exemplary Compd. No. 5 | 0.3 | 82 | 0.76 | 0.07 | 5 |
| 4 | Comparative Compd. (A) | 2.0 | 73 | 0.77 | 0.07 | 6 |
| 5 | Comparative Compd. (B) | 0.5 | 85 | 0.80 | 0.08 | 12 |
| 6 | Comparative Compd. (C) | 1.0 | 77 | 0.76 | 0.07 | 6 |

From Table 1, it can be understood that the DIR couplers of this invention are capable of gamma control with small amounts added, and the images obtained are good without color turbidity by the cyan dyes formed.

Next, the same Samples were stored at 60° C. in 80% RH (Relative Humidity) for 3 days, followed by application of exposure at the same time, and subjected to the same development processing to obtain the results as shown in Table 2. The sensitivity values were shown in terms of the relative values to the untreated Sample 1 as 100.

TABLE 2

| Sample No. | Compound | DIR amount added (mol/100 Ag mols) | S | γ | Fog |
|---|---|---|---|---|---|
| 1 | Control | — | 97 | 2.00 | 0.16 |
| 2 | Exemplary Compd. No. 2 | 0.3 | 83 | 0.75 | 0.09 |
| 3 | Exemplary Compd. No. 5 | 0.3 | 82 | 0.73 | 0.08 |
| 4 | Comparative Compd. (A) | 2.0 | 56 | 0.60 | 0.05 |
| 5 | Comparative Compd. (B) | 0.5 | 83 | 0.77 | 0.08 |
| 6 | Comparative Compd. (C) | 1.0 | 40 | 0.50 | 0.05 |

From Table 2, it can be seen that the Comparative compounds (A) and (C) suffer from marked desensitization and softening of tone after 3 days at 60° C. in 80% RH, indicating decomposition of the compounds, while the compounds of this invention and the Comparative compound (B) are very stable substantially without changes even under such storing conditions.

EXAMPLE 2

On a triacetate film base having a halation preventive layer was provided the following coating. From a solution of 15 g of the compound shown below as the magenta coupler dissolved in 15 g of tricresyl phosphate and 45 ml of ethyl acetate, an emulsion was prepared similarly as in Example 1. The dispersion was added to 1 kg of a green sensitive silver iodobromide emulsion (containing 6 mol % of silver iodide) and incorporated with a film hardener similarly as in Example 1, and the resultant composition was coated on the above film base and dried.

The thus prepared light-sensitive silver halide color photogrhic material is called as Sample 7. In the emulsified diepsersion used in Sample 7 were added Exemplary compounds No. 19 and 30 to provide Samples 8 and 9, respectively. In the emulsified dispersions used in Sample 7 were added the Comparative compounds (D), (E) and (F), and preparations made, coated and dried similarly as in Sample 7 to provide Samples 10, 11 and 12, respectively.

The above Samples were subjected to the same exposure and developing processing similarly as in Example 1 to obtain the results as shown in Table 3.

TABLE 3

| Sample No. | Compound | Amount added (mol/100 Ag mols) | S | γ | Fog | Color turbidity (%) |
|---|---|---|---|---|---|---|
| 7 | Control | — | 100 | 2.10 | 0.17 | 12 |
| 8 | Exemplary Compd. No. 19 | 0.5 | 82 | 0.75 | 0.10 | 12 |
| 9 | Exemplary Compd. No. 30 | 0.3 | 83 | 0.78 | 0.09 | 12 |
| 10 | Comparative Compd. (D) | 3.0 | 70 | 0.72 | 0.10 | 13 |
| 11 | Comparative Compd. (E) | 0.6 | 80 | 0.73 | 0.10 | 20 |
| 12 | Comparative | 0.6 | 82 | 0.74 | 0.10 | 21 |

TABLE 3-continued

| Sample No. | Compound | Amount added (mol/100 Ag mols) | S | γ | Fog | Color turbidity (%) |
|---|---|---|---|---|---|---|
| | Compd. (F) | | | | | |

In Table 3, the color turbidity values are shown in terms of percentage values of Red densities at the Green density of 1.0.

Magenta coupler (as disclosed in U.S. Pat. No. 2,600,788):

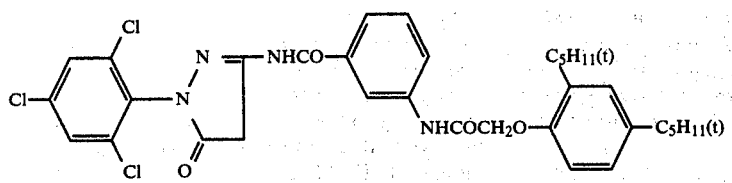

Comparative compound (D) (as disclosed in Japanese Provisional Patent Publication No. 114946/1981):

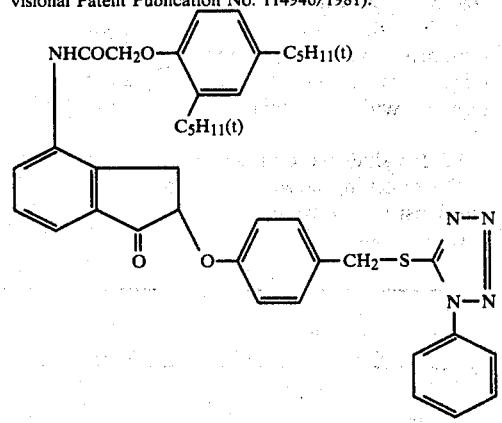

Comparative compound (E) (as disclosed in Japanese Provisional Patent Publication No. 114946/1981):

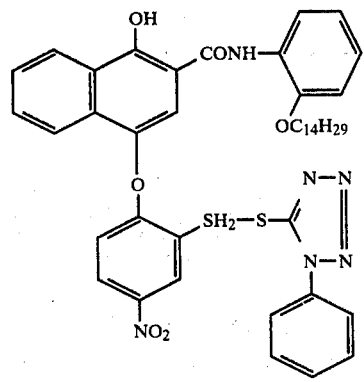

Comparative compound (F) (as disclosed in Japanese Provisional Patent Publication No. 154234/1982):

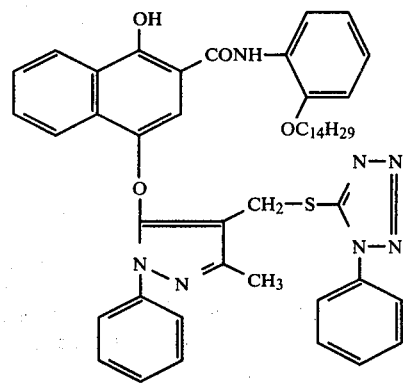

From Table 3, it can be seen that the compounds of this invention are capable of tone control with small amounts added as compared with Comparative compounds (D), (E) and (F), and the images obtained are good without color turbidity as compared with Comparative compounds (E) and (F) which are great in color turbidity.

Next, the same Samples were stored at 60° C. in 80% RH for 3 days, followed by application of exposure processing similarly as in Example 1 to obtain the results as shown in Table 4. The sensitivity values were shown in terms of the relative values to the untreated Sample 7 as 100.

TABLE 4

| Sample No. | Compound | Amount added (mol/Ag mol × 100) | S | γ | Fog |
|---|---|---|---|---|---|
| 7 | Control | — | 95 | 2.00 | 0.19 |
| 8 | Exemplary Compd. No. 19 | 0.5 | 80 | 0.73 | 0.10 |
| 9 | Exemplary Compd. No. 30 | 0.3 | 80 | 0.75 | 0.09 |
| 10 | Comparative Compd. (D) | 3.0 | 72 | 0.70 | 0.09 |
| 11 | Comparative Compd. (E) | 0.6 | 78 | 0.72 | 0.11 |
| 12 | Comparative Compd. (F) | 0.6 | 78 | 0.72 | 0.11 |

Table 4 show that the compounds of this invention are stable after storage at 60° C. in 80% RH.

Next, the Samples 7 to 12 were subjected to wedge exposure by a green light and the same development processings were applied similarly as in Example 1, and graininesses of the processed Samples were measured according to the RMS (Root Mean Square) method.

The results of the RMS granularity at the density 0.7 are shown in Table 5.

On the other hand, a green light was exposed on the Samples 7 to 12 through a wedge varying in space frequency from 3 lines/mm to 100 lines/mm, followed by developing processings similarly as in Example 1, and improved effects of sharpness were examined by determining MTF (Modulation Transfer Function) of the resultant color images with a green light and making comparison between the values of MTF at space frequencies of 10 line/mm and 30 lines/mm. The results are shown in Table 5.

RMS values written were 1000-fold values of the standard deviations of fluctuations in density values which occur during scanning by means of a microdensitometer with a circular scanning orifice diameter of 25μ.

MTF values were indicated as the percentage values of the resolving power based on the input, by carrying out density measurements by means of a slitter with slit widths of 300μ×2μ.

TABLE 5

| | | | | | MTF (%) | |
|---|---|---|---|---|---|---|
| Sample No. | Compound | Amount added (mol/100 Ag mols) | γ | RMS | 10 lines/mm | 30 lines/mm |
| 7 | Control | — | 1.80 | 78 | 100 | 65 |
| 8 | Exemplary Compd. No. 19 | 0.5 | 0.73 | 40 | 121 | 98 |
| 9 | Exemplary Compd. No. 30 | 0.3 | 0.72 | 41 | 118 | 100 |
| 10 | Comparative Compd. (D) | 3.0 | 0.68 | 48 | 102 | 70 |
| 11 | Comparative Compd. (E) | 0.6 | 0.70 | 48 | 115 | 95 |
| 12 | Comparative Compd. (F) | 0.6 | 0.71 | 46 | 114 | 96 |

From Table 5, it can be seen that the compounds of this invention are excellent in both graininess and sharpness as compared with the Comparative compounds, when the same gradation tone was attained for respective samples.

EXAMPLE 3

On a transparent triacetate film base, the following layers were coated successively in the order shown below to prepare Samples 13 to 17 shown below.

First layer: Red sensitive emulsion layer

As a cyan coupler, 10.6 g of 1-hydroxy-N-[4-(2,4-di-tert-amylphenoxy)butyl]-2-naphthoamide was dissolved in 11 ml of tricresyl phosphate and 30 ml of ethyl acetate, and the emulsion was prepared similarly as in Example 1. Then, the dispersion was added to 1 kg of a red sensitive silver iodobromide emulsion (containing 6 mol % of silver iodide), and, as a film hardening agent, 40 ml of 2% solution of 1,2-bis(vinylsulfonyl)ethane (in a mixture of water and methanol at a ratio of 1:1) was added,, followed by coating and drying. The amount of silver coated was 20 mg/dm$^2$ and the coupler mol/Ag mol was 0.1.

Second layer: Intermediate layer

A gelatin layer containing 0.5 g/m$^2$ of gelatin and 0.1 g/m$^2$ of 2,5-di-tert-octylhydroquinone was coated.

Third layer: Green sensitive emulsion layer

As a magenta coupler, 15 g of the coupler employed in Example 2 was dissolved in 15 g of tricresyl phosphate and 45 ml of ethyl acetate, and the emulsion was prepared similarly as in Example 1. The emulsion was added to 1 kg of a green sensitive silver iodobromide (containing 6 mol % of silver iodide) and, with addition of a film hardening agent, the mixture was coated and dried. The amount of silver coated was 20 mg/dm$^2$, with the coupler mol/Ag mol being 0.1, Fourth layer: Protective layer A gelatin layer containing 0.5 g/m$^2$ was coated.

The thus prepares sample was called as Sample 13, and Exemplary compounds Nos. 3 and 24 of this invention were added to the oil component in the third component of Sample 13 to provide Samples 14 and 15, respectively. Comparative compounds (A) and (B) were added to the oil component in the Sample 13 to provide Samples 16 and 17, respectively.

The amount of the development inhibitor releasing compounds was controlled so that the $\gamma_G$ (gamma in the green sensitive layer) may be approximately the same. The thus prepared Samples 13 to 17 were subjected to wedge exposure with a green light, and then to uniform exposure with a red light at a dose so as to give a red density of 2.0, folllowed by the developing processings in the same manner as in Example 1. IIE to the red sensitive layer was examined to obtain the results as shown in Table 6.

IIE to the red sensitive layer was calculated as follows. The red sensitive layer, which is in itself is uniformly exposed to have D=2.0, is inhibited in development of the red sensitive layer corresponding to the density developed in the green sensitive layer through the inter-image effect, and thus shown in terms of the ratio of the red light density decreased. When $D_1$ is given as the red light density at the maximum green light density, the strength of the inter-image can be expressed by $$\left(\frac{2.0 - D_1}{2.0} \times 100\right)$$

That is, the higher is this value, the stronger the inter-image effect to result in improvement in color reproducibility.

TABLE 6

| Sample No. | Compound | Amount added (mol/100 Ag mols) | $\gamma_G$ | IIE (%) |
|---|---|---|---|---|
| 13 | Control | — | 1.80 | 5 |
| 14 | Exemplary Compd. No. 3 | 0.4 | 0.80 | 20 |
| 15 | Exemplary Compd. No. 24 | 0.4 | 0.83 | 19 |
| 16 | Comparative Compd. (A) | 2.0 | 0.80 | 10 |
| 17 | Comparative Compd. (B) | 0.6 | 0.78 | 18 |

From Table 6, the effect of this invention can be understood from the fact that the compounds of this invention can be markedly strengthened in IIE as compared with Comparative compounds (A) and (B).

EXAMPLE 4

A solution of 10 g of a cyan coupler having the structure shown below dissolved in 10 ml of tricresyl phosphate and 30 ml of ethyl acetate was dispersed similarly as in Example 1 and added to the same emulsion and coated on the same support to provide a Sample 18.

On the other hand, into the emulsified dispersion used in Sample 18 were used in combination Exemplary Compd. No. 5 and 9 of this invention in amounts of 0.3 mole per 100 moles of silver, respectively, to provide Samples 19 and 20, respectively. When these samples were subjected to exposure and development processings similarly as in Example 1, Samples 19 and 20 employing the compounds of this invention exhibited good gradation adjustment effect.

Cyan coupler (as disclosed in U.S. Pat. No. 2,474,293):

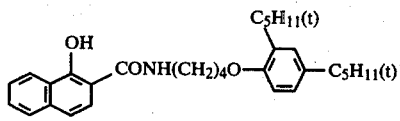

EXAMPLE 5

On a cellulose triacetate film applied with a subbing coating was provided the following coating. As a yellow coupler, 15 g of the compound having the structure as shown below was dissolved in 15 ml of tricresyl phosphate and 45 ml of ethyl acetate, and the resultant solution was mixed with 200 ml of a 5% aqueous gelatin solution containing 20 ml of a 5% aqueous solution of Alkanol B (alkylnaphthalene sulfonate, produced by E. I. Du Pont de Nemours & Company). The mixture was emulsified in a colloid mill to obtain an emulsified product. This dispersion was added to 1 kg of a green sensitive silver iodobromide emulsion (containing 6 mol % of silver iodide) and incorporated with 40 ml of a 2% aqueous solution of 1,2-bis(vinylsulfonyl)ethane as film hardener, followed by coating and drying. (amount of silver coated: 20 mg/dm$^2$, coupler mol/Ag mol=0.1)

The thus prepared light-sensitive silver halide color photographic material is called as Sample 21.

In the emulsified dispersion used in Sample 21, Exemplary compounds Nos. 37 and 40 of this invention were added in amounts of 10 mol % relative to the above magenta coupler, respectively, and preparations made, coated and dried similarly as in Sample 1 to provide Samples 22 and 23, respectively.

In the emulsified dispersion used in Sample 21, the Comparative compounds (G), (H) and (J) shown below were added, respectively, and preparations made, coated and dried similarly as in Sample 21 to provide Samples 24, 25 and 26, respectively.

Magenta coupler (as disclosed in U.S. Pat. No. 2,600,788):

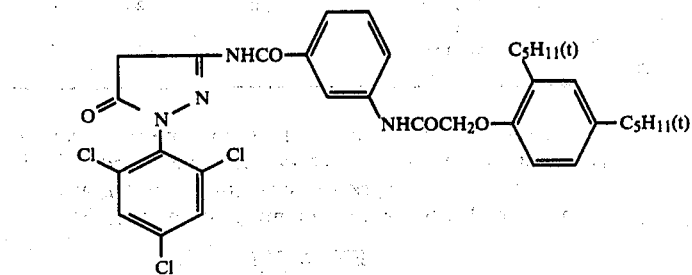

Comparative DAR coupler (G) (as disclosed in Japanese Provisional Patent Publication No. 150845/1982):

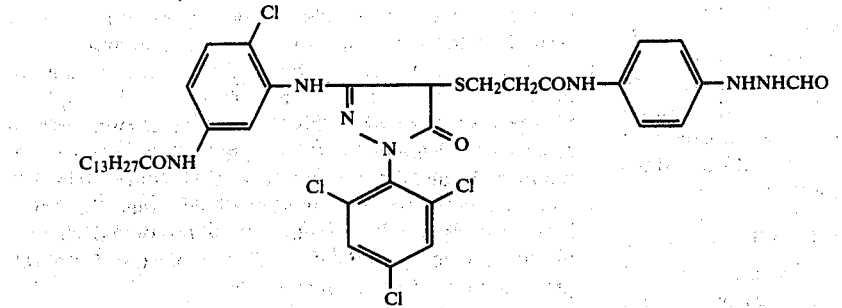

Comparative DAR coupler (H) (as disclosed in Japanese Provisional Patent Publication No. 150845/1982):

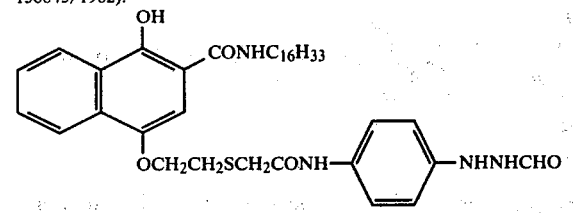

Comparative DAR coupler (J) (as disclosed in Japanese Provisional Patent Publication No. 150845/1982):

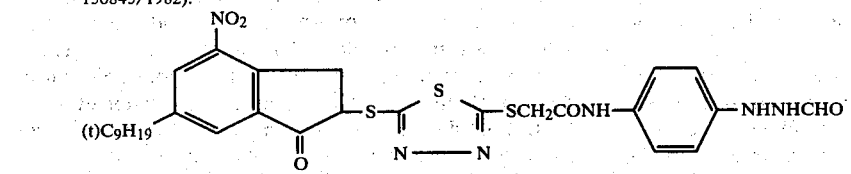

After each of these Samples 21 to 26 was subjected to wedge exposure, color developing processing was applied thereon according to the following processing steps with the use of the following processing compositions.

On the other hand, the same Samples 21 to 26, while being unexposed, were treated at 50° C. in 80% RH for 3 days, and at 55° C. in 10% RH for 3 days, followed by application of exposure and development processings similarly as described above.

| [Processing steps] (38° C.) | Processing time |
|---|---|
| Color developing | 3 min. 15 sec. |
| Bleaching | 6 min. 30 sec. |
| Washing with water | 3 min. 15 sec. |
| Fixing | 6 min. 30 sec. |
| Washing with water | 3 min. 15 sec. |
| Stabilization | 1 min. 30 sec. |

The processing solutions employed in respective processing steps had the compositions shown below:

| [Composition of color developing solution] | |
|---|---|
| 4-Amino-3-methyl-N—ethyl-N—(β-hydroxyethyl)-aniline sulfate | 4.75 g |
| Anhydrous sodium sulfite | 4.25 g |
| Hydroxyamine.½ sulfate | 2.0 g |
| Anhydrous potassium carbonate | 37.5 g |

-continued

| | |
|---|---|
| Sodium bromide | 1.3 g |
| Nitrilotriacetic acid trisodium salt (monohydrate) | 2.5 g |
| Potassium hydroxide | 1.0 g |
| (made up to one liter with addition of water and adjusted to pH 10.0 with potassium hydroxide) | |
| [Composition of bleaching solution] | |
| Ferric ammonium ethylenediamine-tetraacetate | 100.0 g |
| Diammonium ethylenediaminetetraacetate | 10.0 g |
| Ammonium bromide | 150.0 g |
| Glacial acetic acid | 10.0 ml |
| (made up to one liter with addition of water and adjusted to pH 6.0 with ammonia water) | |
| [Composition of fixing solution] | |
| Ammonium thiosulfate (50% aqueous solution) | 162 ml |
| Anhydrous sodium sulfite | 12.4 g |
| (made up to one liter with addition of water and adjusted to pH 6.5 with acetic acid) | |
| [Composition of stabilizing solution] | |
| Formalin (37% aqueous solution) | 5.0 ml |
| Konidax (trade name, produced by Konishiroku Photo Industry, Co., Ltd.) | 7.5 ml |
| (made up to one liter with addition of water) | |

The magenta dye images as obtained above were measured with a green light by means of a densitometer (PD-7R, produced by Konishiroku Photo Industry, Co., Ltd.). The sensitivitities on the same day were given in terms of the relative values to the sensitivity of Sample 21 as 100, while in samples after treatment at 50° C. in 80% RH and at 55° C. in 10% RH, in terms of the relative values to the sensitivity of each sample as 100. The fogging, $\gamma$ and $D_{max}$ measured are also shown in Table 7.

On the other hand, $D_{max}$ portions ($D_G$) obtained by the development on the same day of Samples 21 to 26 were subjected to measurement of densities through a red filter for examination of color turbidity to obtain the results shown in Table 8.

TABLE 8

| Sample No. | Color turbidity ($D_R/D_G \times 100$) |
|---|---|
| 21 | 12 |
| 22 | 12 |
| 23 | 13 |
| 24 | 12 |
| 25 | 20 |
| 26 | 12 |

As apparently seen from Table 8, in the Sample 5 employing Comparative compound (H) which is excellent in reactivity and stable to heat and humidity, color turbidity is noticeably high due to the cyan dye formed from the Comparative compound (H). In contrast, in Samples 22 and 23 employing the compounds of this invention, the color turbidity values are the same as in Sample 21, whereby the dyes formed from the compounds of this invention can be recognized to be flown out of the system.

EXAMPLE 6

On a triacetate film base having a halation preventive layer was provided the followign coating. From a solution of 18 g of a compound having the structure as shown below as the cyan coupler dissolved in 18 g of tricresyl phosphate and 55 ml of ethyl acetate, an emulsion was prepared similarly as in Example 1. The dispersion was added to 1 kg of a red sensitive silver iodobromide emulsion (containing 6 mol % of silver iodide,

TABLE 7

| Sample No. | DAR coupler | On the same day | | | | 50° C., 80% RH treatment | | | | 55° C., 10% RH treatment | | | |
|---|---|---|---|---|---|---|---|---|---|---|---|---|---|
| | | Sensitivity | Fog | $\gamma$ | $D_{max}$ | Sensitivity | Fog | $\gamma$ | $D_{max}$ | Sensitivity | Fog | $\gamma$ | $D_{max}$ |
| 21 | — | 100 | 0.12 | 1.8 | 2.20 | 83 | 0.14 | 1.7 | 2.18 | 89 | 0.13 | 1.8 | 2.21 |
| 22 | Exemplary Compd. No. 37 | 185 | 0.13 | 2.7 | 2.35 | 85 | 0.14 | 2.8 | 2.34 | 92 | 0.13 | 2.8 | 2.32 |
| 23 | Exemplary Compd. No. 40 | 173 | 0.12 | 2.5 | 2.30 | 88 | 0.13 | 2.6 | 2.33 | 92 | 0.12 | 2.6 | 2.30 |
| 24 | Comparative Compd. (G) | 175 | 0.12 | 2.5 | 2.32 | — | 1.47 | — | 2.35 | — | 1.35 | — | 2.31 |
| 25 | Comparative Compd. (H) | 180 | 0.13 | 2.6 | 2.30 | 85 | 0.15 | 2.7 | 2.28 | 89 | 0.13 | 2.6 | 2.32 |
| 26 | Comparative Compd. (J) | 122 | 0.13 | 2.0 | 2.25 | 63 | 1.63 | — | 2.08 | — | 1.56 | — | 2.14 |

From Table 7, it can be understood that the Samples 22 to 25 containing the compounds of this invention and Comparative compounds (G), (H) are each marked in sensitivity elevation and hardened tone and without increase in fogging as compared with Comparative sample 21. In contrast, for Sample 26 containing Comparative compound (J), such effects can scarcely be seen, indicating low reactivity of Comparative compound (J). As for the raw sample storability at 50° C. in 80% RH or at 55° C. in 10% RH, the Samples 24 and 26 containing Comparative compounds (G) and (J) are poor in raw storability with marked increase of fogging, while the Samples employing the compounds of this invention and Comparative compound (H) are very stable to heat and humidity.

mean grain size: 1.02$\mu$) and incorporated with a film hardener similarly as in Example 1, and the resultant composition was coated on the above film base and dried (amount of silver coated: 25 mg/dm$^2$, coupler mol/Ag mol=0.1). The thus prepared light-sensitive silver halide color photographic material is called as Sample 27.

On the other hand, to the above emulsified diepsersion of coupler, Exemplary compound No. 46 of this invention was added in an amount of 10 mol % relative to the above cyan coupler, and the resultant dispersion was added to 1 kg of a red sensitive silver iodobromide emulsion (containing 6 mol % of silver iodide, mean grain size: 0.8$\mu$), and the preparation made, coated and dried similarly as in Sample 27 to provide a Sample 28.

Cyan coupler (as disclosed in Japanese Provisional Patent Publication No. 100087/1982):

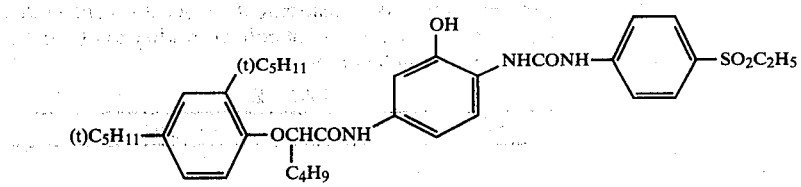

In Samples 27 and 28, the mean grain sizes were adjusted here so that the both Samples may have approximately the same photographic characteristics.

These Samples 27 and 28 were exposed and developed similarly as in Example 5 to obtain the photographic performances as shown in Table 9 in which the results of measurement of the granularity of the dyes at the density 0.7 measured according to the RMS (Root Mean Square) method are also shown.

TABLE 9

| Sample No. | DIR coupler | Color forming property ||||  RMS value |
|---|---|---|---|---|---|---|
| | | Sensitivity | Fog | γ | $D_{max}$ | |
| 27 | — | 100 | 0.08 | 1.42 | 2.10 | 62 |
| 28 | Exemplary compound No. 10 | 110 | 0.09 | 1.51 | 2.18 | 36 |

The sensitivities are shown in terms of the relative values to that of Sample 27 as 100.

From Table 9, it can be seen that, while Samples 27 and 28 exhibit substantially equal photographic characteristics, Sample 28 employing the compound of this invention is clearly improved in graininess as compared with Sample 27, thus indicating a marked effect of the compound of this invention in improvement of granularity.

EXAMPLE 7

Exemplary compound (coupler) No. 51 was weighed in an amount of $2 \times 10^{-2}$ mol, and dissolved in the same weight as that of the coupler, of tricresyl phosphate and three times as much as that of the coupler, of ethyl acetate, and the resultant solution was mixed with 300 ml of a 5% aqueous gelatin solution containing 20 ml of a 5% aqueous solution of Alkanol B (alkylnaphthalene sulfonate, produced by E. I. Du Pont de Nemours & Company). The mixture was emulsified in a colloid mill to obtain a dispersion. This dispersion was added to 1 kg of a green-sensitive silver iodobromide emulsion (containing 6 mol % of silver iodide and 94 mol % of silver bromide) and incorporated with 20 ml of a 2% aqueous solution of 1,2-bis(vinylsulfonyl)ethane as film hardener, followed by coating and drying, to prepare a color light-sensitive material Sample 29. The amount of silver coated was 2 g/m².

Further, by use of Exemplary compounds (couplers) Nos. 61 and 62 in place of Exemplary compound (coupler) No. 51, the above procedure was repeated to prepare Samples 30 and 31.

On the other hand, for comparative purpose, the above procedure was repeated by use of Comparative couplers (K) and (L) to prepare Samples 32 and 33.

Comparative coupler (K) (as disclosed in U.S. Pat. No. 2,600,788):

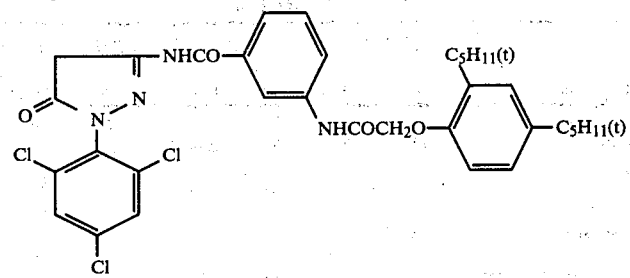

Comparative coupler (L) (as disclosed in Japanese Provisional Patent Publication No. 100087/1982):

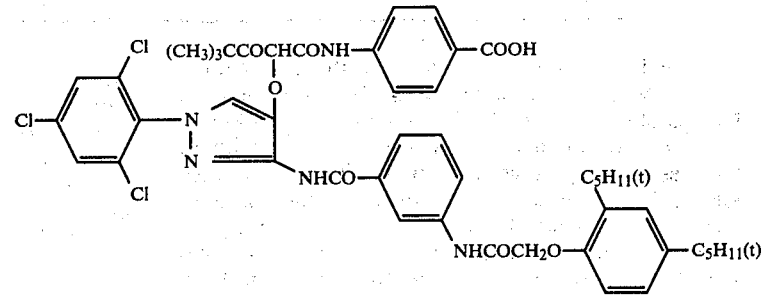

After each of these Samples 29 to 33 was subjected to wedge exposure in a conventional manner, developing processing was applied thereon according to the following processing steps with the use of the following processing compositions.

On the other hand, the same Samples 29 to 33, while being unexposed, were treated at 50° C. in 80% RH for 3 days, and at 55° C. in 10% RH for 3 days, followed by application of exposure and development processings similarly as described above.

| [Processing steps] (38° C.) | Processing time |
|---|---|
| Color developing | 3 min. 15 sec. |
| Bleaching | 6 min. 30 sec. |
| Washing with water | 3 min. 15 sec. |
| Fixing | 6 min. 30 sec. |
| Washing with water | 3 min. 15 sec. |
| Stabilization | 1 min. 30 sec. |

The processing solutions employed in respective processing steps had the compositions shown below:

| [Composition of color developing solution] | |
|---|---|
| 4-Amino-3-methyl-N—ethyl-N—(β-hydroxyethyl)-aniline sulfate | 4.75 g |
| Anhydrous sodium sulfite | 4.25 g |
| Hydroxyamine.½ sulfate | 2.00 g |
| Anhydrous potassium carbonate | 37.50 g |
| Sodium bromide | 1.30 g |
| Nitrilotriacetic acid trisodium salt (monohydrate) | 2.50 g |
| Potassium hydroxide | 1.00 g |
| (made up to one liter with addition of water and adjusted to pH 10.0 with potassium hydroxide) | |
| [Composition of bleaching solution] | |
| Ferric ammonium ethylenediaminetetraacetate | 100.0 g |
| Diammonium ethylenediaminetetraacetate | 10.0 g |
| Ammonium bromide | 150.0 g |
| Glacial acetic acid | 10.0 ml |
| (made up to one liter with addition of water and adjusted to pH 6.0 with ammonia water) | |
| [Composition of fixing solution] | |
| Ammonium thiosulfate (50% aqueous solution) | 162 ml |
| Anhydrous sodium sulfite | 12.4 g |
| (made up to one liter with addition of water and adjusted to pH 6.5 with acetic acid) | |
| [Composition of stabilizing solution] | |
| Formalin (37% aqueous solution) | 5.0 ml |
| Konidax (trade name, produced by Konishiroku Photo Industry, Co., Ltd.) | 7.5 ml |
| (made up to one liter with addition of water) | |

The magenta dye images as obtained above were measured with a green light by means of a densitometer (PD-7R, produced by Konishiroku Photo Industry, Co., Ltd.). The sensitivities on the same day were given in terms of the relative values to the sensitivity of Sample (33) as 100, while in samples after treatment at 50° C. in 80% RH and at 55° C. in 10% RH, in terms of the relative values to the sensitivity of each sample as 100. The fogging and $D_{max}$ measured are also shown in Table 10.

From Table 10, it can be understood that the Samples 29, 30 and 31 containing the compounds of this invention exhibit clearly better results with higher sensitivity and $D_{max}$ than the Sample employing the Comparative coupler (L). Moreover, while the coupler of this invention is a 6-equivalent coupler, it exhibits performances comparable with Comparative coupler (K) which is a 4-equivalent coupler. In raw sample storability by the treatment at 50° C. in 80% RH or at 55° C. in 10% RH, Sample 33 employing Comparative coupler (L) is poor in raw storability to be deteriorated in color formation. In contrast, the Samples employing the couplers of this invention are found to be very stable to heat and humidity.

On the other hand, the $D_{max}$ portions ($D_G$) of the Samples 29 to 33 were measured by measurements of densities through a blue filter ($D_B$) and then through a red filter ($D_R$) for examination of color turbidities to obtain the results shown in Table 11.

TABLE 11

| | Color turbidity | |
|---|---|---|
| Sample No. | $D_B/D_G \times 100$ | $D_R/D_G \times 100$ |
| 29 | 19 | 12 |
| 30 | 21 | 13 |
| 31 | 18 | 12 |
| 32(Comparative) | 18 | 12 |
| 33(Comparative) | 27 | 14 |

As apparently seen from Table 11, color turbidity is observed due to the yellow pigment from the blocking group in the Sample employing Comparative coupler (L) and therefore inferior in alkali solubility characteristic.

In contrast, the Sample employing the couplers of this invention exhibit color turbidity values substantially equal to that of the Sample employing Comparative coupler (K), thus indicating flow-out from the system of the cyan dyes formed by the blocking groups.

The Samples 29 to 33 under unexposed state were also left to stand for 3 days in a dark room in a sealed vessel containing an aqueous 1% formaldehyde without being contacted with the solution. These Samples and the untreated Samples for comparative purpose were exposed and developed, followed by measurements of sensitivity and the maximum density to determine formalin resistance (%) [Treated sample/Untreated sample $\times$ 100].

The results obtained are shown in Table 12.

TABLE 10

| Sample No. | Compound (coupler) | On the same day | | | Treatment (50° C., 80% RH) | | | Treatment (55° C., 10% RH) | | |
|---|---|---|---|---|---|---|---|---|---|---|
| | | Sensitivity | Fog | $D_{max}$ | Sensitivity | Fog | $D_{max}$ | Sensitivity | Fog | $D_{max}$ |
| 29 | Exemplary Compd. No. 51 | 108 | 0.13 | 1.61 | 88 | 0.15 | 1.58 | 87 | 0.14 | 1.58 |
| 30 | Exemplary Compd. No. 61 | 115 | 0.10 | 1.63 | 89 | 0.11 | 1.61 | 90 | 0.10 | 1.58 |
| 31 | Exemplary Compd. No. 63 | 119 | 0.11 | 1.59 | 91 | 0.12 | 1.57 | 90 | 1.11 | 1.58 |
| 32 | Comparative Coupler (K) | 120 | 0.16 | 1.74 | 80 | 0.18 | 1.70 | 83 | 0.17 | 1.67 |
| 33 | Comparative Coupler (L) | 100 | 0.10 | 1.56 | 65 | 0.13 | 1.31 | 71 | 0.14 | 1.46 |

TABLE 12

| Sample No. | Formalin resistance (%) | |
|---|---|---|
| | Sensitivity | $D_{max}$ |
| 29 | 92 | 94 |
| 30 | 94 | 96 |
| 31 | 91 | 93 |
| 32 | 70 | 52 |
| 33 | 90 | 88 |

From Table 12, it can be seen that the Samples employing the couplers of this invention are clearly more excellent than the Sample employing the Comparative coupler (K).

EXAMPLE 8

Exemplary compound (coupler) No. 57 was weighed in an amount of $2 \times 10^{-2}$ mol, and a coupler dispersion was prepared in the same manner as in Example 7. The coupler dispersion was mixed with 1 kg of a photographic emulsion containing $14 \times 10^{-2}$ mol of a red-sensitive silver iodobromide (containing 8 mol % of silver iodide and 92 mol % of silver bromide), admixed with 20 ml of a 2% aqueous solution of 1,2-bis(vinylsulfonyl)ethane as a film hardener, and coated on a triacetate film base to prepare Sample 34 of a color light-sensitive material. The amount of silver coated in Sample 34 was 3.5 g/m².

Further, except for using Comparative coupler (M) in place of Exemplary compound (coupler) No. 57 and changing the amount of silver coated to 2 g/m₂, entirely the same procedure as describe above was repeated to prepare Sample 35.

Comparative coupler (M) (as disclosed in Japanese Patent Publication No. 37857/1982):

$$(t)C_5H_{11}\text{—}\bigcirc\text{—}OCHCONH\text{—}\bigcirc\text{—}NHCONH\text{—}\bigcirc\text{—}CN$$
$$(t)C_5H_{11}\qquad\qquad OH\qquad\qquad C_4H_9$$

The amounts of silver coated were adusted here in Samples 34 and 35 so that both may have approximately the same photographic characteristics.

These Samples 34 and 35 were exposed and developed similarly as in Example 7 to obtain the photographic performances shown in Table 13. These developed Samples were subjected to measurement of granularity of the dyes at the density of 0.7 with a red light according to RMS (Root Mean Square method) method to obtain the results also shown in the same Table.

TABLE 13

| Sample No. | DIR coupler | Color forming property | | | | RMS value |
|---|---|---|---|---|---|---|
| | | Sensitivity | Fog | γ | $D_{max}$ | |
| 34 | Exemplary coupler No. 57 | 97 | 0.12 | 1.25 | 2.21 | 34 |
| 35 | Comparative coupler (M) | 100 | 0.13 | 1.30 | 2.07 | 55 |

The sensitivities are shown in terms of the relative values to that of Sample 35 as 100.

From Table 13, it can be seen that, while Samples 34 and 35 exhibit substantially equal photographic characteristics, Sample 34 employing the compound of this invention is clearly improved in graininess as compared with Sample 35, thus indicating a marked effect of the compound of this invention in improvement of graininess.

We claim:

1. A light-sensitive silver halide color photographic material containing a compound represented by formula (I):

Formula (I)

[Naphthalene structure with substituents O—G, $R_1$, $R_2$, and X]

wherein G is a hydrogen atom or a blocking group which is eliminated from the compound of formula (I) through hydrolysis or intramolecular nucleophilic substitution during development; $R_1$ is an organic group having up to 16 carbon atoms and at least one substituent selected from the group consisting of carboxyl, sulfo and hydroxyl, which may also form a salt; $R_2$ is a hydrogen atom or a water soluble acidic group; and X is (a) a development accelerator group; or
(b) a TIME-PUG group;

wherein TIME is a timing group and PUG is a photographically useful group wherein said TIME-PUG group is eliminated from the compound of formula (I) through the reaction of the compound of formula (I) with an oxidized product of a color forming developing agent and thereafter the PUG group can be released from said TIME-PUG group, said compound of formula (I) and a cyan dye formed through the reaction of said compound with said oxidized product of said color forming developing agent being soluble in alkali.

2. The light-sensitive silver halide color photographic material of claim 1, wherein X is said TIME-PUG group.

3. The light-sensitive silver halide color photographic material of claim 2, wherein TIME is a group selected from following formulae (II) and (IV):

$$-Y-\underset{Z}{\bigcirc}-\underset{R_{15}}{\overset{R_{14}}{\underset{|}{C}}}-$$

Formula (II)

wherein Z is an atomic group necessary for completion of a benzene ring, a substituted benzene ring, a naphthalene ring or a substituted naphthalene ring; Y is —O—, —S— or $$-\underset{|}{\overset{R_{16}}{N}}-$$

and is bonded to the coupling position of the compound of formula (I); $R_{14}$, $R_{15}$ and $R_{16}$ are each selected from the group consisting of a hydrogen atom, an alkyl group, and an aryl group and the group

is substituted at an ortho position or a para position relative to Y and is bonded to a heteroatom of said PUG group;

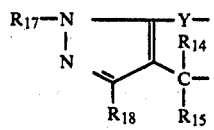

wherein Y, $R_{14}$ and $R_{15}$ are the same as defined in formula (II), respectively; $R_{17}$ is selected from the group consisting of a hydrogen atom, an alkyl group, an aryl group, an acyl group, a sulfonyl group, an alkoxycarbonyl group and a heterocyclic group residue; and $R_{18}$ is selected from the group consisting of a hydrogen atom, an alkyl group, an aryl group, a heterocyclic group residue, an alkoxy group, an amino group, an acid amide group, a sulfonamide group, a carboxyl group, an alkoxycarbonyl group, a carbamoyl group and a cyano group; wherein the TIME group of formula (IV) is bonded through Y to the coupling position of the compound of formula (I) and to a heteroatom of PUG through the group

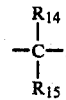

4. The light-sensitive silver halide color photographic material of claim 1, wherein TIME is a group of formula (V) which is capable of releasing PUG through an intramolecular nucleophilic reaction:

Formula (V)

wherein Nu is a nucleophilic group having an oxygen, sulfur or nitrogen atom enriched in electrons and is bonded to the coupling position of the compound of formula (I); E is an electrophilic group having an electron deficient group selected from the group consisiting of a carbonyl group, a thiocarbonyl group, a phosphinyl group and a thiophosphinyl group and is bonded to a heteroatom of PUG; and A is a bonding group which sterically correlates Nu with E and, wherein said Nu is released from the compound of formula (I) and then is subjected to an intramolecular nucleophilic substitution reaction to form a 3-membered to 7-membered ring, thereby releasing PUG.

5. The light-sensitive silver halide color photographic material of claim 1, wherein PUG is selected from the group consisting of development inhibitors, development accelerators, bleaching inhibitors, bleaching accelerators, developers, fixers, silver halide solvents, silver-complex forming agents, film hardeners, tanning agents, color controllers, fogging agents, fogging inhibitors, chemical or optical sensitizers, desensitizers, photographic dyes or precursors thereof and couplers.

6. The light-sensitive silver halide color photographic material of claim 1, wherein X is an acccelerator group represented by formula (VII):

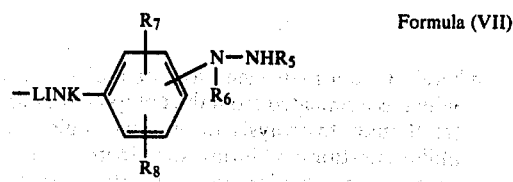

wherein LINK represents a divalent connecting group, $R_5$ is selected from the group consisting of a formyl group, an acyl group, a sulfonyl group, an alkoxycarbonyl group, a carbamoyl group, and a sulfamoyl group; $R_6$ is selected from the group consisting of a hydrogen atom, an acetyl group, an ethoxycarbonyl group and a methanesulfonyl group; and each of $R_7$ and $R_8$ is selected from the group consisting of a hydrogen atom, a lower alkyl group, a lower alkoxy group and a halogen atom.

7. The light-sensitive silver halide color photographic material of claim 1, wherein said compound is represented by formula (VI):

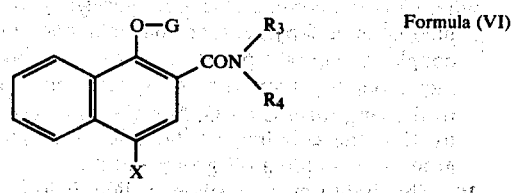

wherein $R_3$ is a hydrogen atom or an alkyl group having 1–4 carbon atoms, $R_4$ is selected from the group consisting of a carboxylalkyl group having up to 12 carbon atoms, a sulfoalkyl group having up to 12 carbon atoms, a hydroxyalkyl group having up to 12 carbon atoms, a substituted phenyl group, a substituted naphthyl group, and a 5-membered or 6-membered substituted heterocyclic group wherein said substituents are at least one member selected from the group consisting of carboxyl, sulfo and hydroxyl, said substitutents being bound directly to said substituted groups or through an alkylene group having 1 to 4 carbon atoms or through a phenylene group; wherein $R_3$ and $R_4$ taken togehter may form a nitrogen containing 5-membered or 6-membered ring substituted with at least one member selected from the group consisting of carboxyl, sulfo and hydroxyl.

8. The light-sensitive silver halide color photographic material of claim 7, wherein said substituted groups are further substituted with at least one substituent selected from the group consisting of halogen, nitro, cyano, an alkyl group having 1–4 carbon atoms, an alkoxyl group having 1–4 carbon atoms, and alkylamino.

9. A light-sensitive slver halide color photographic material containing a compound represented by formula (I):

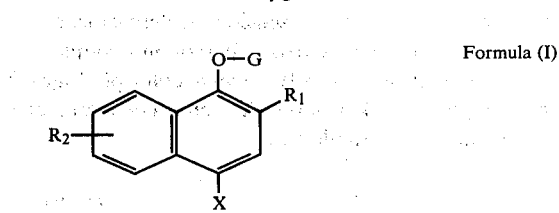

Formula (I)

wherein G is a hydrogen atom or a blocking group which is eliminated from the compound of formula (I) though hydrolysis or intramolecular nucleophilic substitution during development; $R_1$ is an organic group having up to 16 carbon atoms and at least one substituent group selected from the group consisting of carboxyl, sulfo and hydroxyl, which may also form a salt; $R_2$ is a hydrogen atom or a water soluble acidic group; and X is represented by formula (VIII):

Formula (VIII)

wherein Q is a non-metallic atom necessary for completion of a 5-pyrazolone magenta dye forming coupler group or a phenol cyan dye forming coupler group together with an oxygen atom adjacent to the ring formed by Q; * in the ring completed by Q is the coupling position; $R_9$ is a hydrogen atom or a coupling-off group and n is 1 or 2.

10. The light-sensitive silver halide color photographic material of claim 1, wherein the organic group having up to 16 carbon atoms represented by $R_1$ is selected from the group consisting of a carbamoyl group, a sulfamoyl group, an acyl group, an aryl sulfonyl group, an aryl group and a heterocyclic group containing at least one substituent selected from the group consisting of carboxyl, sulfo and hydroxyl.

11. The light-sensitive silver halide color photographic material of claim 1, wherein the water soluble acidic group represented by $R_2$ is selected from the group consisting of carboxyl, sulfo, carboxyalkyl, sulfoalkyl and carboxylalkylamino.

12. The light-sensitive silver halide color photographic material of claim 1, wherein the blocking group represented by G is selected from the group consisting of aliphatic carbonyl, aromatic carbonyl, aliphatic sulfonyl and aromatic sulfonyl.

13. The light-sensitive silver halide color photographic material of claim 1, wherein the blocking group represented by G is represented by the formula:

$$-E^1-X^1-Nu^1P$$

wherein $E^1$ is an electrophilic group, $Nu^1P$ is a precursor of a nucleophilic group convertible to a nucleophilic group under alkaline conditions; and $X^1$ is a bonding group which sterically correlates $E^1$ with $Nu^1P$ so that an intramolecular nucleophilic substitution reaction may occur which cleaves the bond between $E^1$ and the oxygen atom of the compound to which $E^1$ is bonded after $Nu^1P$ has been converted to a nucleophilic group.

14. The light-senstive silver halide color photographic material of claim 9, wherein the coupling-off group is selected from the group consisting of halogen, alkoxy, aryloxy, heterocycloxy, sulfonyloxy, acyloxy, heterocyclyl, thiocyano, alkylthio, arylthio, heterocyclylthio, sulfonamide, phosphonyloxy and arylazo.

15. The light-sensitive silver halide color photographic material of claim 9, wherein the organic group having up to 16 carbon atoms represented by $R_1$ is selected from the group consisting of a carbamoyl group, a sulfamoyl group, an acyl group, an aryl sulfonyl group, an aryl group and a heterocyclic group containing at least one substituent selected from the group consisting of carboxyl, sulfo and hydroxyl.

16. The light-sensitive silver halide color photographic material of claim 9, wherein the water soluble acidic group represented by $R_2$ is selected from the group consisting of carboxyl, sulfo, carboxyalkyl, sulfoalkyl and carboxylalkylamino.

17. The light-sensitive silver halide color photographic material of claim 9, wherein the blocking group represented by G is selected from the group consisting of aliphatic carbonyl, aromatic carbonyl, aliphatic sulfonyl and aromatic sulfonyl.

18. The light-sensitive silver halide color photographic material of claim 9, wherein the blocking group represented by G is represented by the formula:

$$-E^1-X^1-Nu^1P$$

wherein $E^1$ is an electrophilic group, $Nu^1P$ is a precursor of a nucleophilic group convertible to a nucleophilic group under alkaline conditions; and $X^1$ is a bonding group which sterically correlates $E^1$ with $Nu^1P$ so that an intramolecular nucleophilic substitution reaction may occur which cleaves the bond between $E^1$ and the oxygen atom of the compound to which $E^1$ is bonded after $Nu^1P$ has been converted to a nucleophilic group.

19. The light-sensitive silver halide color photographic material of claim 1, wherein G is selected from the group consisting of a hydrogen atom and a blocking group represented by the formula:

$$-E^1-X^1-Nu^1P$$

wherein $E^1$ is an electrophilic group, $Nu^1P$ is a precursor of a nucleophilic group convertible to a nucleophilic group under alkaline conditions; and $X^1$ is a bonding group which sterically correlates $E^1$ with $Nu^1P$ so that an intramolecular nucleophilic substitution reaction may occur which cleaves the bond between $E^1$ and the oxygen atom of the compound to which $E^1$ is bonded after $Nu^1P$ has been converted to a nucleophilic group;

wherein $R_1$ is selected from the group consisting of a carbamoyl group, a sulfamoyl group, an acyl group, an aryl sulfonyl group, an aryl group and a heterocyclic group containing at least one substituent selected from the group consisting of carboxyl, sulfo and hydroxyl; and wherein $R_2$ is selected from the group consisting of carboxyl, sulfo, carboxyalkyl, sulfoalkyl and carboxyalkylamino.

20. The light-sensitive silver halide color photographic material of claim 9, wherein G is selected from the group consisting of a hydrogen atom and a blocking group represented by the formula:

$$-E^1-X^1-Nu^1P$$

wherein $E^1$ is an electrophilic group, $Nu^1P$ is a precursor of a nucleophilic group convertible to a nucleophilic group under alkaline conditions; and $X^1$ is a bonding group which sterically correlates $E^1$ with $Nu^1P$ so that an intramolecular nucleophilic substitution reaction may occur which cleaves the bond between $E^1$ and the oxygen atom of the compound to which $E^1$ is bonded after $Nu^1P$ has been converted to a nucleophilic group;

wherein $R_1$ is selected from the group consisting of a carbamoyl group, a sulfamoyl group, an acyl group, an aryl sulfonyl group, an aryl group and a heterocyclic group containing at least one substituent selected from the group consisting of carboxyl, sulfo and hydroxyl; and wherein $R_2$ is selected from the group consisting of carboxyl, sulfo, carboxylalkyl, sulfoalkyl and carboxylalkylamino.

* * * * *